United States Patent
Cise et al.

(10) Patent No.: US 7,150,727 B2
(45) Date of Patent: *Dec. 19, 2006

(54) APPARATUS AND METHOD FOR PREVENTING FREE FLOW IN AN INFUSION LINE

(75) Inventors: David Cise, Riverton, UT (US); David J. McNally, Salt Lake City, UT (US); Kent F. Beck, Layton, UT (US)

(73) Assignee: Zevex, Inc., Salt Lake City, UT (US)

( * ) Notice: Subject to any disclaimer, the term of this patent is extended or adjusted under 35 U.S.C. 154(b) by 173 days.

This patent is subject to a terminal disclaimer.

(21) Appl. No.: 10/317,027

(22) Filed: Dec. 11, 2002

(65) Prior Publication Data

US 2003/0125674 A1    Jul. 3, 2003

Related U.S. Application Data

(63) Continuation-in-part of application No. 09/836,850, filed on Apr. 16, 2001, which is a continuation-in-part of application No. 09/569,332, filed on May 11, 2000, now Pat. No. 6,595,950.

(51) Int. Cl.
*A61M 5/00* (2006.01)

(52) U.S. Cl. .............. 604/246; 604/247; 604/256; 604/30

(58) Field of Classification Search ............ 604/118–9, 604/119, 249, 254–256, 30–1, 48, 245–9; 137/192, 455, 843, 853; 222/556
See application file for complete search history.

(56) References Cited

U.S. PATENT DOCUMENTS

| | | | |
|---|---|---|---|
| 584,091 A * | 6/1897 | Leidich | ........ 137/849 |
| 2,471,623 A | 5/1949 | Hubbell | |
| 2,518,165 A | 8/1950 | Millard | |
| 2,858,095 A | 10/1958 | Harris et al. | |
| 2,999,499 A | 9/1961 | Willet | |
| 3,213,882 A | 10/1965 | Beatty | |
| 3,329,391 A | 7/1967 | Deane | |
| 3,985,140 A | 10/1976 | Harris | |
| 3,998,364 A | 12/1976 | Hollander | |
| 4,037,596 A | 7/1977 | LeFevre et al. | |
| 4,063,555 A * | 12/1977 | Ulinder | ............ 604/83 |
| 4,065,093 A | 12/1977 | Phillips | |
| 4,106,675 A * | 8/1978 | Taylor | ............ 222/556 |
| 4,142,645 A | 3/1979 | Walton | |
| 4,160,383 A * | 7/1979 | Rauschenberger | ....... 73/863.85 |
| 4,230,151 A | 10/1980 | Jonsson | |
| 4,236,880 A | 12/1980 | Archibald | |
| 4,381,591 A | 5/1983 | Barger et al. | |
| 4,382,453 A | 5/1983 | Bujan et al. | |
| 4,425,116 A | 1/1984 | Bilstad et al. | |

(Continued)

FOREIGN PATENT DOCUMENTS

EP    00150666 A1    9/1984

(Continued)

*Primary Examiner*—Kevin Sirmons
*Assistant Examiner*—Andrew Gilbert
(74) *Attorney, Agent, or Firm*—Bateman IP Law Group

(57) ABSTRACT

An apparatus and method for preventing free flow through an infusion set utilizes an occluder disposed within the infusion set to selectively prevent flow therethrough. The occluder may be responsive to a pressure differential within the infusion set or may respond to compression of the infusion set. When a pair of occluders are used in sequence, an in-line pump may be formed.

21 Claims, 21 Drawing Sheets

U.S. PATENT DOCUMENTS

| | | | |
|---|---|---|---|
| 4,453,295 A | 6/1984 | Laszczower | |
| 4,498,843 A | 2/1985 | Schneider et al. | |
| 4,524,802 A | 6/1985 | Lawrence et al. | |
| 4,527,588 A | 7/1985 | Tseo et al. | |
| 4,559,045 A | 12/1985 | Danby et al. | |
| 4,579,553 A * | 4/1986 | Urquhart et al. | 604/246 |
| 4,596,557 A * | 6/1986 | Pexa | 604/284 |
| 4,624,663 A | 11/1986 | Danby et al. | |
| 4,634,092 A | 1/1987 | Daniell et al. | |
| 4,645,489 A | 2/1987 | Krumme et al. | |
| 4,689,043 A | 8/1987 | Bisha | |
| 4,728,324 A | 3/1988 | Steigerwald et al. | |
| 4,730,635 A | 3/1988 | Linden | |
| 4,913,401 A | 4/1990 | Handke | |
| 4,935,010 A | 6/1990 | Cox et al. | |
| 4,960,259 A | 10/1990 | Sunnanvader et al. | |
| 5,020,562 A | 6/1991 | Richmond et al. | |
| 5,022,422 A | 6/1991 | di Palma | |
| 5,083,561 A | 1/1992 | Russo | |
| 5,098,406 A * | 3/1992 | Sawyer | 137/843 |
| 5,151,019 A | 9/1992 | Danby et al. | |
| 5,219,327 A | 6/1993 | Okada | |
| 5,232,193 A | 8/1993 | Skakoon | |
| 5,238,218 A | 8/1993 | Mackal | |
| 5,257,978 A | 11/1993 | Haber et al. | |
| 5,265,847 A | 11/1993 | Vorhis | |
| 5,336,174 A | 8/1994 | Daoud et al. | |
| 5,395,351 A * | 3/1995 | Munsch | 215/355 |
| 5,396,925 A | 3/1995 | Poli | |
| 5,474,544 A * | 12/1995 | Lynn | 128/912 |
| 5,531,713 A * | 7/1996 | Mastronardi et al. | 604/158 |
| 5,578,070 A * | 11/1996 | Utterberg | 210/239 |
| 5,704,584 A | 1/1998 | Winterer et al. | |
| 5,807,312 A | 9/1998 | Dzwonkiewicz | |
| 5,810,323 A | 9/1998 | Winterer et al. | |
| 5,826,621 A * | 10/1998 | Jemmott | 137/853 |
| 6,017,332 A * | 1/2000 | Urrutia | 137/192 |
| 6,092,695 A | 7/2000 | Loeffler | |
| 6,183,447 B1 * | 2/2001 | Urrutia | 604/247 |
| 6,196,992 B1 * | 3/2001 | Keilman et al. | 604/131 |
| 6,209,538 B1 * | 4/2001 | Casper et al. | 128/200.24 |
| 6,398,758 B1 * | 6/2002 | Jacobsen et al. | 604/104 |
| 6,398,780 B1 | 6/2002 | Farley et al. | |

FOREIGN PATENT DOCUMENTS

| | | |
|---|---|---|
| EP | 0150666 A1 | 9/1984 |
| EP | 0 150 666 | 8/1985 |
| EP | 0 423 978 | 4/1991 |
| EP | 0 423 978 A2 | 4/1991 |
| EP | 0423978 A2 | 4/1991 |
| EP | 0 483 794 | 5/1992 |
| EP | 0 483 794 A1 | 5/1992 |
| EP | 0483794 A1 | 5/1992 |

* cited by examiner

APPARATUS AND METHOD FOR PREVENTING FREE FLOW IN AN INFUSION LINE

RELATED APPLICATIONS

The present application is a continuation-in-part of U.S. patent application Ser. No. 09/836,850, filed Apr. 16, 2001, which is a continuation-in-part of U.S. patent application Ser. No. 09/569,332, filed May 11, 2000 now U.S. Pat. No. 6,595,950.

BACKGROUND OF THE INVENTION

1. Field of the Invention

The present invention relates to an apparatus and method for preventing free flow during enteral or parenteral administration solutions through an infusion line. More particularly, the present invention relates to an occluder/valve and method of use for infusion sets and the like, wherein the occluder/valve prevents undesirable free-flow of solution through the infusion set while allowing controlled flow through the infusion set.

2. State of the Art

The use of infusion sets to administer solutions to patients is well known in the medical arts. Infusion sets are used for both enteral and parenteral applications. Enteral feeding pumps are used to provide patients with nutrition and medication when they are unable, for a variety of reasons, to eat normally. Parenteral (intravenous) solutions are provided to patients to ensure adequate hydration and to provide needed nutrients, minerals and medication. Often, the infusion set is placed in a free standing arrangement in which gravity forces the solution into the patient. The rate at which the solution enters the patient can be roughly controlled by various clamps, such as roller clamps, which are currently available on the market.

In many applications, it is necessary to precisely control the amount of solution which enters the patient. When this is the case, a regulating device, such as an enteral feeding pump, is placed along the infusion set to control the rate at which the solution is fed to the patient. In applications where a pump, etc., is used, the clamps used to regulate flow are typically opened to their fullest extent to prevent the clamp from interfering with the proper functioning of the pump. The clamp is opened with the expectation that the enteral feeding pump will control fluid flow through the infusion set.

It is not uncommon, however, for emergencies or other distractions to prevent the medical personnel from properly loading the infusion set in the enteral feeding pump. When the infusion set is not properly loaded in the pump and the clamp has been opened, a situation known as free-flow often develops. The force of gravity causes the solution to flow freely into the patient unchecked by the pump or other regulating device. Under a free-flow condition, an amount of solution many times the desired dose can be supplied to the patient within a relatively short time period. This can be particularly dangerous if the solution contains potent medicines and/or the patient's body is not physically strong enough to adjust to the large inflow of solution.

Numerous devices have been developed in an attempt to prevent free flow conditions. Such devices, however, typically add significantly to the overall cost of the infusion set and some provide only marginal protection against free flow.

Thus, there is a need for a device that prevents a free-flow condition while allowing controlled flow through the infusion set. There is also a need for such a device which prevents free-flow if an infusion set is not properly mounted in a pump or other regulating means. Furthermore, there is a need for a device which prevents free-flow and which is inexpensive and easy to use.

SUMMARY OF THE INVENTION

It is an object of the present invention to provide an apparatus and method for occluding infusion sets to prevent an accidental free-flow condition.

It is another object of the present invention to provide an occluder which is simple to make and use.

It is another object of the present invention to provide such an occluder which is inexpensive and thus disposable.

It is still another object of the present invention to provide an occluder which occludes fluid flow through the infusion set unless the infusion set is properly loaded in a flow control mechanism such as an enteral feeding pump.

It is still yet another object of the present invention to provide such an occluder which allows for a simple manual override of the occluding function.

It is still yet another aspect of the present invention to provide an occluder which functions as a valve to effectively control fluid flow through a flexible conduit.

One or more of the above and other objects of the invention are realized in an apparatus and method for preventing free flow in an infusion set. In accordance with one aspect of the invention, an occluder is disposed within the infusion set. The occluder is configured to prevent free flow of fluids in the infusion set past the occluder. The occluder is also configured, however, to selectively allow solutions to pass by the occluder which are pumped by an enteral feeding pump and the like.

In accordance with one embodiment of the invention, the occluder is formed by a stop placed in the tubing of the infusion set. The stop limits flow through the tube by limiting flow around and/or through the stop when the solution is subject to flow due to gravity. However, when greater pressures are placed on the solution, such as those produced by a pump, the solution is able to flow around and/or through the stop, thereby delivering the solution to the patient.

In accordance with another embodiment of the present invention, an occluding valve is disposed in the infusion set. The valve prevents free flow through the infusion set due to gravity, while allowing controlled flow of solution through the infusion set.

In accordance with another aspect of the invention, the occluder is configured to stop fluid flow until the infusion set has been properly loaded into a control mechanism such as a pump. Once properly placed, the interaction between the occluder and the infusion set effectively opens the infusion set to allow solution to flow therethrough.

In accordance with still another aspect of the present invention, the occluder can be formed integrally with the infusion set or can be formed of independent piece(s) which are then placed in the infusion set to selectively occlude the flow of solution therethrough.

In accordance with still yet another aspect of the invention, the occluder can function as a valve to selectively allow fluid flow therethrough. In one embodiment, a pair of occluders and infusion line can be used in conjunction with a piston or other force applicator to form a linear peristaltic pump which delivers predetermined amounts of fluid to a patient.

In accordance with still yet another aspect of the present invention, the occluder and infusion line can be formed to nest in and be opened by a conventional fluid flow pump.

BRIEF DESCRIPTION OF THE DRAWINGS

The above and other objects, features, and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims. Additionally, while various embodiments will achieve some of the objectives set forth above, it will be understood that some embodiments may not achieve all of the objectives and the objectives should not be viewed as limiting the pending claims.

Figure 1:
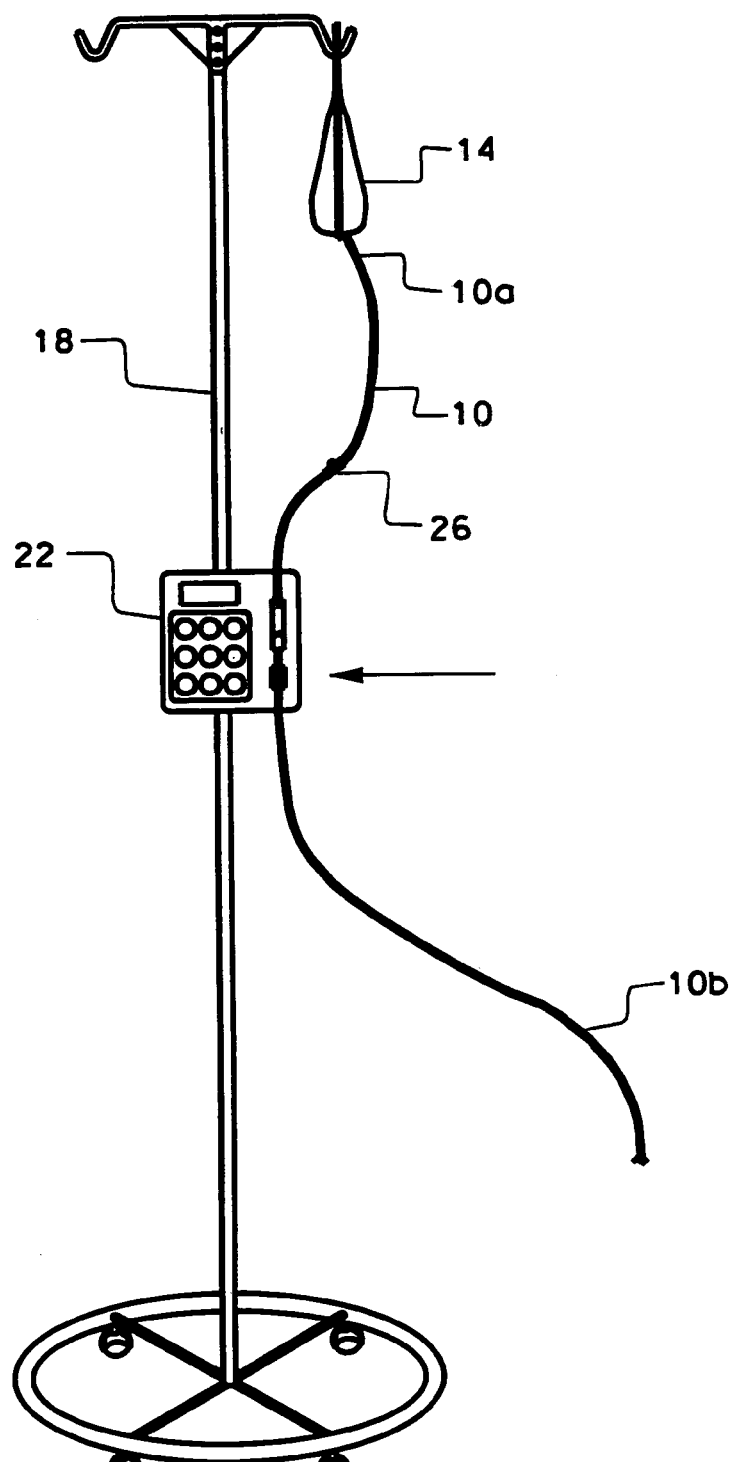
FIG. 1 shows an perspective view of an infusion set made in accordance with the prior art.

Referring to FIG. 1, there is shown a perspective view of an infusion set 10 and related structures in accordance with the teachings of the prior art. Disposed at one end 10a of the infusion set 10 is a bag 14 for holding parenteral or enteral solutions. Typically, the bag 14 is supported by a stand 18 which holds the bag approximately 6 feet off the floor.

The opposing end 10b of the infusion set 10 is connected to a patient (not shown). In a parenteral use, the end of the infusion set 10 would have a needle attached thereto which extends into the patient's venous system. In a enteral use, the end 10b would typically have a fitting which attached to a balloon catheter (not shown) mounted in a stoma in the patient's stomach. The end may also be connected to a nasoenteric feeding tube.

Solution flows under gravity from the upper end 10a of the infusion set 10 to the lower end 10b. The pressure on the fluid is 0.433 psi per foot. Thus, if the bag 14 is disposed five feet higher than the patient, the pressure at the lower end 10b of the infusion set 10 is about 2.165 psi. From the extreme height of 8 feet to the floor, the solution in the infusion set 10 can reach approximately 3.5 psi.

To control the flow of solution through the infusion set 10, the infusion set is typically mounted through a flow control portion of a pump 22. The pump 22 selectively allows a metered amount of solution to pass distally (downstream) from the pump. This can be accomplished in multiple ways. For example, many enteral feeding pumps are peristaltic pumps which have a rotor which engages the infusion set 10 with a plurality rollers. Each partial rotation of the rotor allows a predetermined dose to pass to the patient. By controlling the rate at which the rotor turns, the pump can provide highly accurate doses of the solution.

Other pumps known in the art control solution flow through the infusion set 10 by a plurality of fingers which engage the infusion set. By controlling the position and frequency of the engagement of the fingers against the infusion set 10, a highly accurate dose can be provided to the patient.

While the pump 22 controls the solution flow through the infusion set 10 when the infusion set is properly loaded, failure to load the infusion set properly in the pump can quickly result in a free flow condition in which the solution flows uncontrolled through the infusion set. To prevent free flow, a clamp 26 is disposed along the infusion set 10. Typically, the clamp 26 is disposed above the pump 22. One common type of clamp 26 is a roller clamp which allows some control over the presence of flow and flow volume through the infusion set 10. Other clamps simply provide on/off control.

While the infusion set 22 should be mounted in the pump 22 prior to or immediately after opening the clamp, this is not always done. There are many situations in a hospital or nursing home setting in which the nurse or physician is called away or otherwise distracted prior to proper placement of the infusion set 10. If the clamp has already been opened, the result is that the solution in the bag 18 flows uncontrolled into the patient.

In many situations, the free flow of the solution will cause no real threat to the patient. In some situations, however, free flow can cause serious injury or even death to the patient. For example, a critically ill patient may suffer severe shock if a large amount of solution were to suddenly flow into his or her body. Likewise, a patient receiving heavily medicated solution may be seriously injured if a solution that was designed to be delivered over a number of hours were delivered in a few minutes.

To resolve such concerns, pinch clips may be disposed on the infusion set 10. The pinch clip automatically closes the infusion set unless it is properly mounted in the infusion set 10. An example of such a pinch clip is disclosed in U.S. Pat. No. 5,810,323.

While pinch clip occluders are a significant advantage over the possibility of free flow, they are relatively expensive to make. While such an occluder may only cost ten to twenty cents, using a new occluder with every infusion set adds a proportionally significant amount to the cost of an infusion set. Thus, there is a need to find an apparatus and method for preventing free flow in an infusion set which is reliable and which is less expensive than the prior art.

Figure 2A:
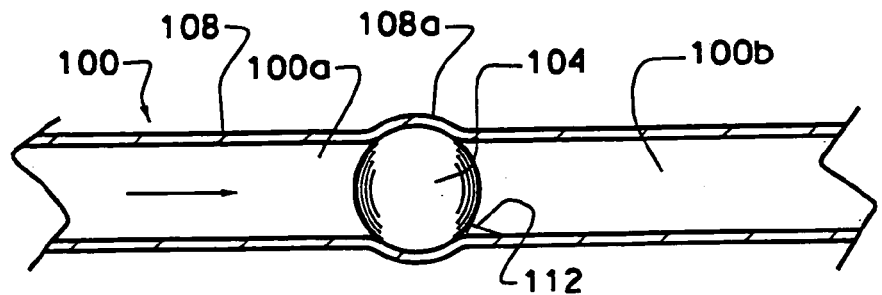
FIG. 2A shows a fragmented, side cross-sectional view of an apparatus and method for preventing free-flow through an infusion set in the form of an occluder mounted in an infusion set with the occluder and infusion set in a closed configuration.

Turning now to FIG. 2A, there is shown a fragmented, cross-sectional of an infusion set, generally indicated at 100, with a stop or occluder 104 disposed therein. The infusion set 100 is formed by an elongate tube 108 made of a flexible, resilient material such as silicone rubber, latex , polyurethane, neoprene or numerous similar medical grade materials. (In light of the present disclosure, those skilled in the art will appreciate that the present invention may be used in nonmedical contexts as well. In such situations, the tube may be made of materials which are not medical grade.)

The occluder 104 has an exterior diameter which is slightly larger than the interior diameter of the tube forming the infusion set 100. This causes a portion 108a of the tube to stretch slightly as is passes over the occluder 104.

The occluder 104 prevents flow through the infusion set 100 based on gravity. Thus, the size of the occluder 104 will depend on the material used to form the infusion set. In a presently preferred embodiment, the infusion set 100 is formed from a tube made of silicone rubber. The tube has a wall thickness of approximately 0.038 inches and an inner diameter of approximately 0.130 inches. The occluder 104 is preferably formed out of a plastic (e.g. acrylonitrile butyl styrene (ABS), acrylic (PMMA), polycarbonate, etc.) or a stainless steel ball bearing having an outer diameter of 0.141 inches.

Because the occluder 104 is larger than the interior diameter of the infusion set 100, solution which is under only the force of gravity will back-up behind the occluder and not pass. To prevent the occluder 104 from gradually working its way downstream, a projection 112 can be formed in the infusion set 100 or, as explained in detail below, the occluder may be fastened to a connector or some other stationary structure.

Figure 2B:
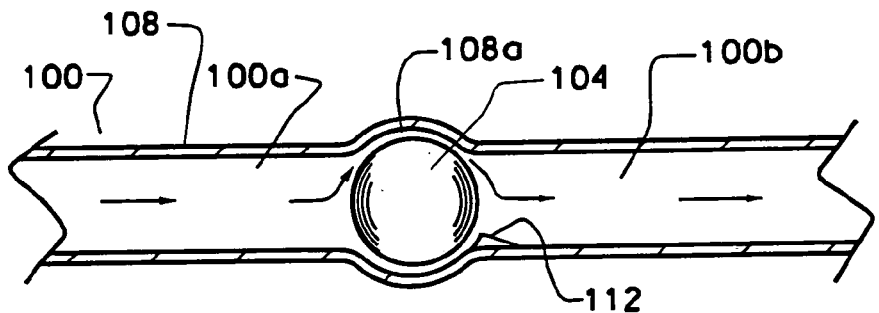
FIG. 2B shows a fragmented, side cross-sectional view similar to that of FIG. 2A, wherein the occluder and infusion set are in an open configuration.

Because the infusion set 100 is formed by an elongate, resilient tube 108, increases in pressure will cause the interior diameter of the tube to expand. When the tube 108 expands sufficiently, the portion 108a of the tube which passes over the occluder 104 allows the solution to flow around the occluder and into the distal part 100b of the infusion set 100 as shown in FIG. 2B.

Preferably, the occluder 104 and infusion set 100 are selected so that up to 4 psi can be maintained upstream of the occluder, i.e. in the proximal portion of the infusion set, before the portion 108a of the elongate tube 108 extending over the occluder will expand sufficiently to allow any clinically significant amount of solution to pass.

While solution hanging in the bag 18 may develop 2 to 3 psi due to gravity, it will not have enough pressure to pass by the occluder 104 without application of some external force. In contrast, an enteral feeding pump or other type of pump will typically generate between 5 and 15 psi. When the solution is pressurized to 5 to 15 psi by the pump, the solution is under sufficient pressure to go around the occluder 104 for delivery to the patient. In other words, if the infusion set 100 is not properly mounted in the pump so that the pump will generate a higher pressure in the proximal part 100a of the infusion set, the occluder 104 inhibits flow to the patient. Thus, there can be no free flow while accommodating flow of solution to the patient when the infusion set 100 is properly mounted in the pump.

Figure 2C:
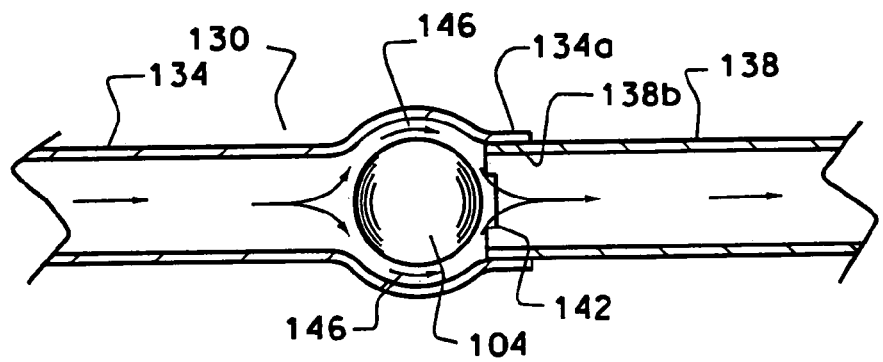
FIG. 2C shows a fragmented, side cross-sectional view of an alternate occluder/infusion set configuration made in accordance with the principles of the present invention.

Turning now to FIG. 2C, there is shown a fragmented, side cross-sectional view of an alternate configuration of an infusion set, generally indicated at 130, and the occluder 104. As with the previous embodiment, the occluder 130 is formed by a small sphere, typically formed of a biologically inert plastic or stainless steel. The infusion set 130 is formed of a first tube 134 and a second tube 138. The first tube 134 is formed of a resilient polymer or silicone so that the tube may expand with pressure. The second tube 138 is typically slightly smaller than the first tube 134 so that the distal end 134a of the first tube can be attached to the exterior of the proximal end 138a of the second tube.

To ensure that the occluder 104 does not advance distally into the second tube 138, the second tube 138 is preferably formed from a material which is semi-resilient or nonresilient and therefore will not accommodate advancement of the occluder 104. To prevent the proximal end 138a of the second tube 138 from forming a seal with the occluder 104, the proximal end preferably has one or more indentations 142 or contours formed therein. The indentations 142 or contours ensure that liquid will be able to flow around the occluder 104 even if the occluder is pressed firmly against the proximal end 138a of the second tube 138.

When pressures less than about 4 psi are disposed proximally from the occluder 104, the first tube 134 engages the occluder and prevents liquid from flowing down stream. Once the pressure on the proximal side of the occluder 104 exceeds approximately 4 psi, the distal end 134a of the first tube 134 expands and allows liquid to flow by in the manner demonstrated by arrows 146. Once the pressure subsides, the first tube 134 returns to its original size and liquid flow terminates until the pressure again is raised above the threshold.

In use, the infusion set 130 and occluder 104 prevent free flow unless the infusion set is placed in engagement with a pump that can generate sufficient psi to compel flow around the occluder. Once past the occluder 104, the pressure of the liquid quickly falls to a conventional level and there is no danger to the patient.

Figure 3E:
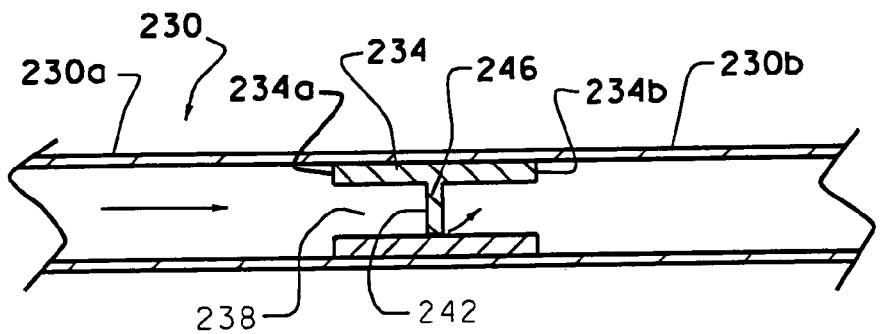
FIG. 3E shows a fragmented, side cross-sectional view of still yet another embodiment of an occluder and infusion set made in accordance with the principles of the present invention.
Figure 3A:
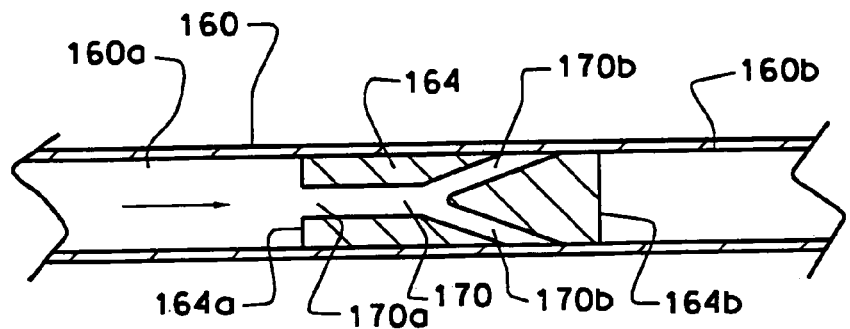
FIG. 3A shows a fragmented, side cross-sectional view of an alternate apparatus and method for preventing free-flow through an infusion set in accordance with the principles of the present invention.

Turning now to FIG. 3A, there is shown a fragmented, cross-sectional view of another embodiment of principle of the present invention. An infusion set 160 has a proximal portion 160a and a distal portion 160b. Disposed between the proximal portion 160a and the distal portion 160b is an occluder or stop 164. The stop 164 is disposed in the infusion set 160 to selectively prevent flow from the proximal portion 160a to the distal portion 160b.

The stop 164 includes a proximal end 164a and a distal end 164b. Beginning at the proximal end 164 is a channel 170. As shown in FIG. 3A, the channel has a proximal portion 170a and two distal portions 170b which are in fluid communication with the proximal portion. While the proximal portion 170a is disposed in continuous communication with the interior of the proximal portion 160a, each of the distal portions 170b of the stop 164 are typically disposed in communication with the sidewall of the infusion set 160. The sidewall of the infusion set 160 normally prevents fluid flow out of the distal portions 170b of the channel 170.

Preferably, the sidewall will have sufficient resistance to expansion that a pressure of about 4 psi can be placed in the channel 170 without causing the infusion set 160 to radially distend or expand. Thus, if the pressure in the proximal portion 160a of the infusion set 160 is below about 4 psi, the liquid will not flow through the stop 164.

As shown in FIG. 3A, the stop 164 is relatively long. To maintain itself in place, the stop 164 frictionally engages the sidewall defining the infusion set 160. By providing a stop 164 which is long, greater surface area is provided to engage the sidewall and prevent the stop 164 from being slowly moved downstream.

Figure 3B:
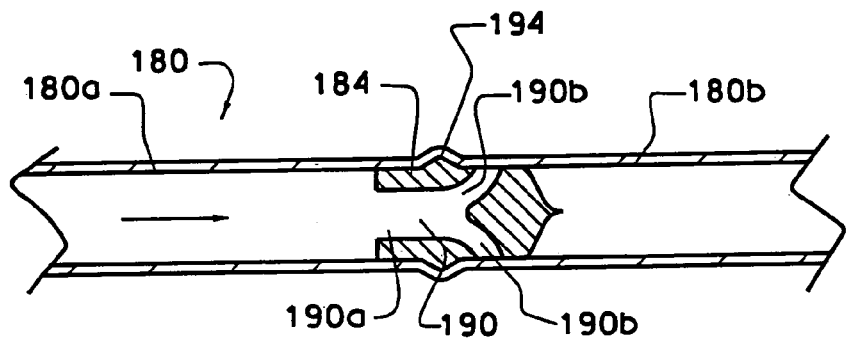
FIG. 3B shows a fragmented, cross-sectional view of an alternate occluder embodiment, with the occluder and infusion set being disposed in a closed configuration.

Turning now to FIG. 3B, there is shown a fragmented, side cross-sectional view of an infusion set, generally indicated at 180. The infusion set 180 includes a proximal (upstream) end 180a and a distal (downstream) end 180b which are separated by an occluder or stop 184. The stop 184 is similar to the stop 164 shown in FIG. 3A in that it has a channel 190 with a proximal portion 190a and a pair of distal portions 190b.

Rather than relying on an elongate body and frictional engagement with the sidewall of the infusion set 180, the stop 184 has at least one projection 194 which extends outwardly from the stop to engage the sidewall of the infusion set and prevent advancement. Preferably, the projection 194 is formed by an annular projection, or a plurality of spaced projections extending radially outwardly from the stop 184.

Figure 3C:
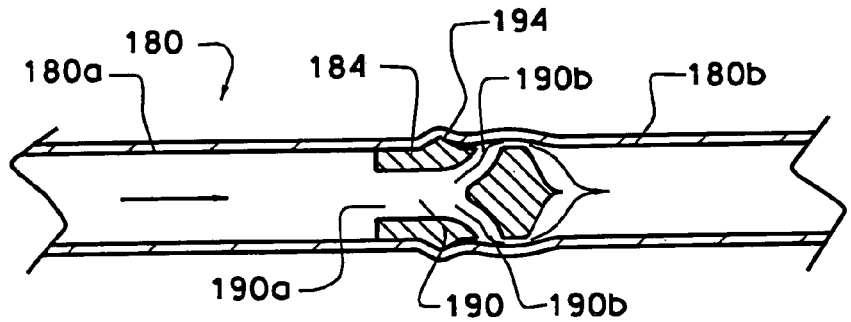
FIG. 3C shows a cross-sectional view of the occluder embodiment of FIG. 3A with the occluder and infusion set being disposed in an open configuration.

Turning now to FIG. 3C, there is shown a cross-sectional view of the infusion set 180 and stop 184 of FIG. 3B. As the pressure in the proximal portion 180a of the infusion set 180 increases to greater than about 4 psi, the infusion set will distend radially. This allows liquid contained in the proximal portion 180a of the infusion set 180 to flow into the proximal portion 190a of the channel 190, out the distal portions 190b of the channel and into the distal portion 180b of the infusion set. Once the pressure drops below about 4 psi, the infusion set 180 will retract and the flow in the channel 190 will be terminated as the sidewall of the infusion set covers the distal portions 190b of the channel 190.

In such a manner, the embodiments shown in FIGS. 3A through 3C prevent free flow by preventing liquid flow under 4 psi. Once the infusion set 180 is properly mounted in the pump, the increased pressure created by rotation of the rotor (or other pressure source) overcomes the restriction to flow imposed by the stop 184. When combined with the control provided by the various types of infusion pumps, the occluder or stop 164 or 184 enables a predetermined amount of liquid to flow through infusion set 160 or 180 while preventing the dangers of free flow conditions.

Figure 3D:
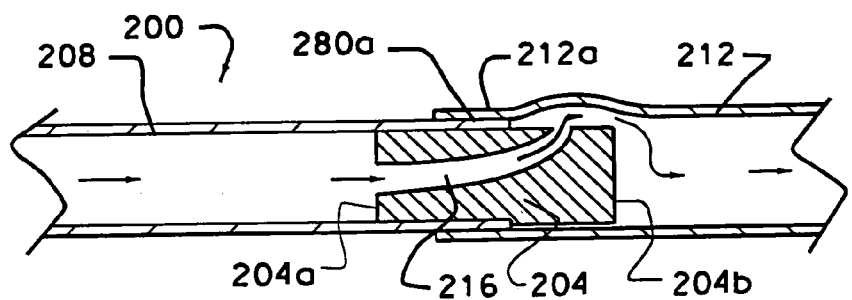
FIG. 3D shows a fragmented, side cross-sectional view of another embodiment of an occluder and infusion set made in accordance with the principles of the present invention.

FIG. 3D shows a side cross-sectional view of yet another embodiment of an infusion set, generally indicated at 200, having an occluder or stop 204 disposed therein. The infusion set 200 includes a proximal portion formed by a first tube 208 and a distal portion formed by a second tube 212. The proximal end 212a of the second tube 212 is mounted about the exterior of the distal end 208a of the first tube 208.

Disposed at the distal end 208a of the first tube 208 and the proximal end 212a of the second tube 212 is the stop 204. The stop 204 has a channel 216 extending from a proximal end 204 of the stop to a radially lateral position adjacent the distal end 204b of the stop. Thus, the channel is in fluid communication with liquid in the first tube 208, but is normally isolated from the interior of the second tube 212.

When pressures in the first tube exceed about 4 psi, the proximal end 212a of the second tube 212 radially expands, thereby opening the distal end of the channel 216 and allowing liquid to flow into the distal portion of the infusion set formed by the second tube 212.

By positioning the stop 204 at the ends of two tube segments, the stop can be adhesively attached to either of the tubes to prevent distal movement of the stop. This can be accomplished without interfering with the ability of the stop to prevent flow below about 4 psi, while allowing pressures above about 4 psi cause liquid to pass through the infusion set.

While the embodiments of FIGS. 3A through 3D show embodiments in which the proximal end of the channel is in continuous communication with the upstream flow and the distal end of the channel is normally closed, the stop 164, 184 or 204 could be rotated so that the proximal or upstream portion of the channel is normally closed by the sidewall of the infusion set 160, 180 or 200 and the distal portion of the channel is always in communication with the distal portion of the infusion set.

FIG. 3E shows yet another embodiment of an infusion set, generally indicated at 230, and an occluder 234. The occluder 234 is disposed in the infusion set 230 so as to divide the infusion set 230 into a proximal, upstream portion 230a and a distal, downstream portion 230b.

The occluder 234 has a channel 238 which extends from a proximal end 234a of the occluder to the distal end 238b so as to form a passageway through which an infusion liquid, such as enteral feeding solution, may pass. A wall 242 is disposed along the channel 238 to selectively prevent flow through the channel. In accordance with the principles of the present invention, the wall 242 is pivotably attached to the occluder 234 in such a manner that the wall will not move to allow liquid flow through the channel until the proximal, upstream pressure exceeds 4 psi. (While described as requiring a threshold upstream pressure, in light of the present disclosure those skilled in the art will appreciate that the wall will move based on a pressure differential between the proximal and distal portions of the infusion set. Thus, the same effect could be generated by developing a vacuum downstream from the occluder 234). Those skilled in the art will appreciate that the above embodiments could be designed for other thresholds as well.

Once the desired pressure threshold has been reached, the wall 242 will pivot and open the channel 238 to flow. Once the pressure drops, the wall 242 will pivot closed in accordance with one method of use. In accordance with another method of use, however, the wall 242 can have a score 246 formed therein. The wall 242 is designed to remain occluding the infusion set 230 until the pressure threshold is exceeded. Once deflected out of the way, the wall may not return to its original position even after the pressure drop. Because the pressure increase necessary to move the wall 242 is generated by the pump (not shown), the infusion set 230 must have been properly loaded in the pump for the wall to open. When the infusion set 230 is properly loaded in the pump, the pump will prevent free flow. Thus, if the infusion set 230 is properly loaded in the pump, the occluder does not need to continue to prevent free flow.

Figure 4A:
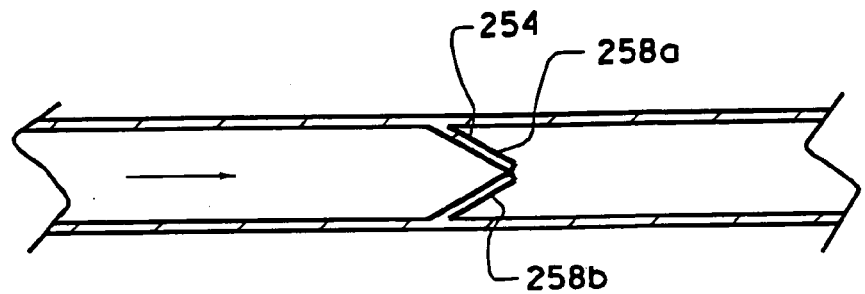
FIG. 4A shows fragmented, side cross-sectional view of another embodiment of an occluder and infusion set with the occluder in a closed configuration.
Figure 4B:
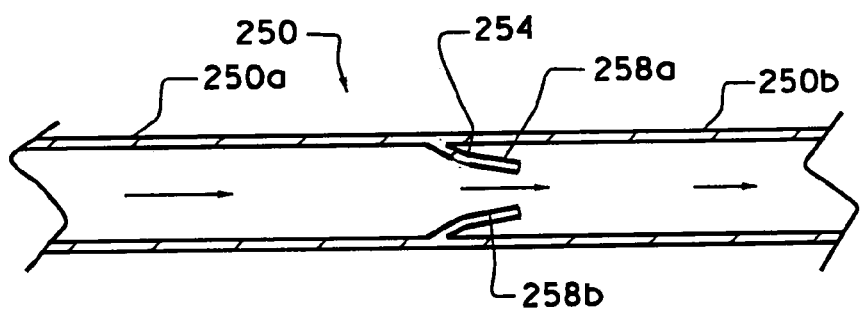
FIG. 4B shows a cross-sectional view of the embodiment of FIG. 4A in an open configuration.

Turning now to FIGS. 4A and 4B, there are shown fragmented, side cross-sectional views of yet another embodiment of the present invention. An infusion set, generally indicated at 250 has an occluder 254 in the form of a duckbill valve formed therein to divide the infusion set 250 into a proximal, upstream portion 250a and a distal, downstream portion 250b. The occluder 254 is formed of two vanes 258a and 258b which are biased into engagement with one another.

When the pressure in the proximal portion 250a of the infusion set 250 is less than about 4 psi, the biasing of the vanes 258a and 258b keep them in contact as shown in FIG. 4A. Once the pressure in the proximal portion 250a exceeds about 4 psi, the pressure forces the valves 258a and 258b away from each other, thereby allowing an infusion liquid to flow through the occluder 254 and into the distal portion 250b of the infusion set 250 as shown in FIG. 4B. In order for the occluder 254 to work in such a manner, it is preferable for the vanes 258a and 258b to extend distally as they engage one another. However, the occluder 254 could be made so that the vanes extend proximally and then buckle once the threshold pressure has been passed.

The occluder 254 is shown as being molded integrally with the infusion set 250. Such a configuration prevents any concern as to whether the occluder 254 may move during use. However, it is feasible to also form such an occluder 254 as a separate unit and then position it within the infusion set 250. The occluder 254 could be held in place with adhesives or merely a friction fit.

Figure 5A:
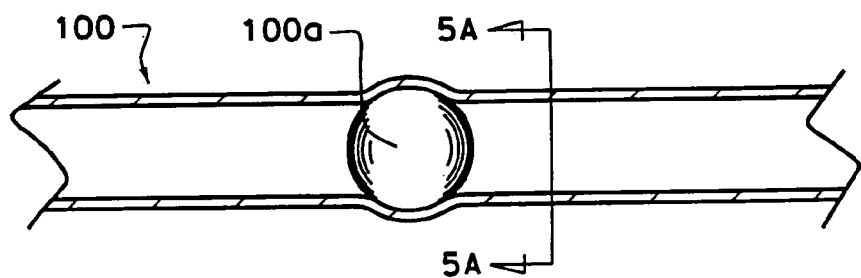
FIG. 5A shows a fragmented side cross-sectional view of an occluder and infusion set made in accordance with one aspect of the present invention with the occluder and infusion set being in a closed position.

Turning now to FIG. 5A there is shown a fragmented, side cross-sectional view of an infusion set, generally indicated at 300, with an occluder 304 disposed therein. Similar to the embodiment shown in FIG. 2A, the infusion set 300 is made of conventional silicone tubing or some other resilient or semi-resilient material, such as latex, polyurethane, etc.

Figure 5B:
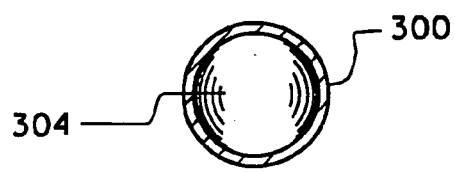
FIG. 5B shows a cross-sectional view taken along plane 5A—5A of FIG. 5A.

FIG. 5B shows a cross-sectional view of the infusion set 300 and occluder 304 taken along the plane A—A in FIG. 5A. As shown, the tube defining the infusion set 300 forms a seal around the occluder 304 and prevents liquid from passing between the occluder and the tube forming the infusion set.

Figure 5C:
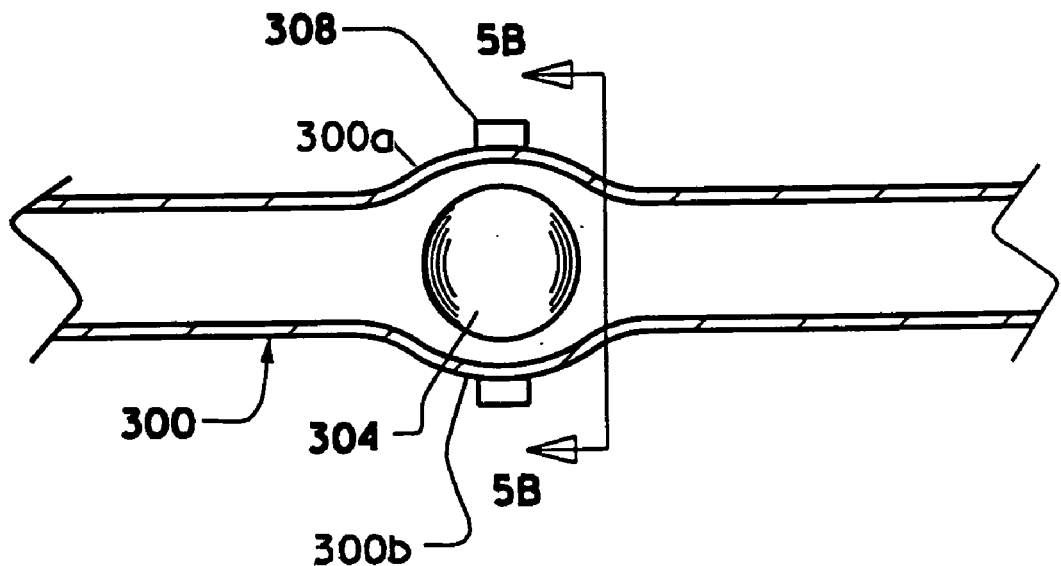
FIG. 5C shows a fragmented, side cross-sectional view of an infusion set with an occluder disposed therein, with the infusion set being mounted in a control mechanism to maintain the infusion set and occluder in an open configuration.

Turning now to FIG. 5C, there is shown a side cross-sectional view of the infusion set 300 and the occluder 304. Disposed behind the infusion set 300 at the location of the occluder 304 is a wall 308. As will be discussed in additional detail below, the wall 308, the occluder 304 and the infusion set 300 form a compression valve for selectively allowing liquid to flow through the infusion set.

Figure 5D:
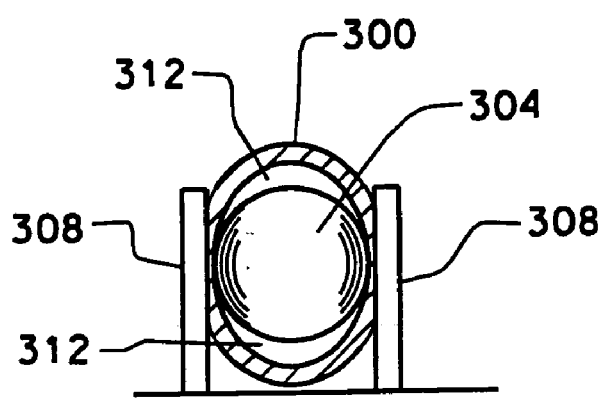
FIG. 5D shows a cross-sectional view taken along the plane 5B—5B of FIG. 5C.

FIG. 5D shows a cross-sectional view of the infusion set 300 and the occluder 304 taken along the plane B—B in FIG. 5C. The infusion set 300 and occluder 304 have been mounted between opposing walls 308 which are spaced apart a distance slightly smaller than the outer diameter of the infusion set. As the infusion set 300 is placed between the opposing walls 308, the sides of the tubing forming the infusion set are compressed and held against the occluder 304. This compression also causes the top and bottom 300a and 300b portions of the tube to extend radially outwardly from the occluder 304, thereby opening a flow path 312 above and below the occluder. The flow paths 312 enable liquid in the infusion set 300 to flow around the occluder 304 and to flow to the patient.

In the event that the infusion set 300 and occluder 304 are pulled out from between the opposing walls 308, the tube forming the infusion set 300 will return to the position shown in FIGS. 5A and 5B, thereby terminating flow through the infusion set. Thus, the configuration shown in FIGS. 5A through 5D prevents free flow of infusion liquids through the infusion set 300 so long as the infusion set and occluder 304 are properly mounted between the walls 308 (or some analogous engagement surfaces). The infusion set 300 and occluder 304 are typically positioned between the walls 308 as the infusion set is being loaded into the pump (not shown). Once properly loaded, the pump controls flow through the infusion set 300 and prevents free flow.

Figure 5E:
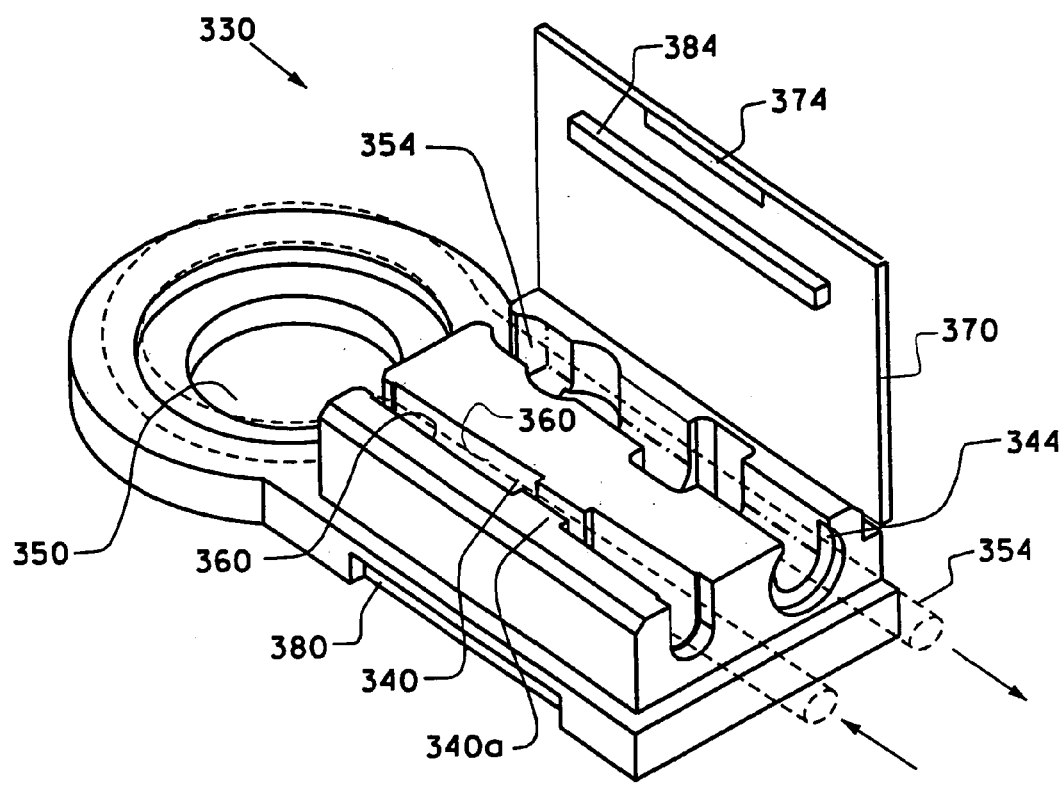
FIG. 5E shows a perspective view of a housing of a control mechanism as may be used to hold the infusion set and occluder in an open position as shown in FIG. 5D.

Turning now to FIG. 5E, there is shown a perspective view of a housing of an enteral feeding pump, generally indicated at 330, made in accordance with one aspect of the present invention. The housing 330 includes a pair of channels 340 and 344 for holding a portion of an infusion set tube, such as those discussed with respect to FIGS. 3A through 5D. In use, the tube is placed in one channel 340, wrapped about a motor unit (not shown) which is placed in the opening 350, and then positioned in the second channel 344. If a conventional infusion set is not properly wrapped about the motor unit (or properly installed in other types of pumps) and placed in the channels 340 and 344, a free-flow condition may develop. However, the present invention prevents such a situation from developing.

As shown in FIG. 5E in broken lines, the infusion set 354 is mounted in the first and second channels 340 and 344. At least a portion 340a of the channel 340 is sufficiently narrow to form walls, similar to walls 308 in FIGS. 5A through 5D, which compress the sides of the tube forming the infusion set 354, thereby creating a flow path around the occluder (not shown) in the infusion set. If desired, the entire length of the walls 360 which form the channel 340 could be sufficiently close together to compress the infusion set 354 and thereby open flow.

FIG. 5E also shows a cover 370 which is connected to the housing 330. The cover 370 is pivotable with respect to the housing 330 and includes a catch 374 which engages a groove 380 on the housing. When the cover 370 is closed and the catch 374 engaged in the groove 380, the infusion set 354 is securely held in the housing 330 and it is unlikely that the infusion set may be pulled from the pump.

Rather than having the walls 360 of the channel 344 compress the sides of the infusion set 354 to form a compression valve with the sides of the infusion set 354, a projection 384 can be mounted on the cover 370 so that it is in alignment with the infusion set. When the cover closes, the projection 384 applies a downward force on the infusion set 354 thereby forming an open compression valve with the flow channels being disposed in horizontal alignment, rather than vertical alignment as shown in FIG. 5D. Thus, liquid flowing through the infusion set 354 passes around the sides of the occluder, as opposed to above and below the occluder.

It will be appreciated in light of the present disclosure, that when a projection is used to engage the occluder, the occluder need not be held in a channel. Rather, the infusion set 354 must only be engaged on generally opposing sides so as to open at least one flow path around the occluder, or sufficient pressure must be exerted to cause the infusion set to expand and open a flow path.

As long as the catch 374 on the cover 370 engages the groove 380 on the housing 330, or the projection 384 is maintained in engagement with the infusion set 354 at the location of the occluder, the compression valve will remain open. If the cover 370 is opened, the force holding the compression valve open is gone and the infusion set 354 will retract into the closed position shown in FIGS. 5A and 5B, thereby preventing free flow through the infusion set 354.

Figure 6A:
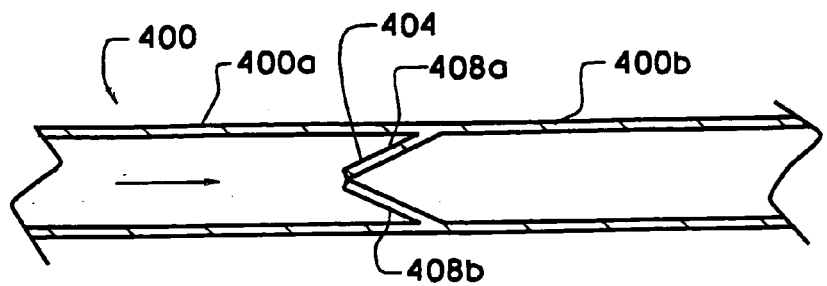
FIG. 6A shows a fragmented, side cross-sectional view of an infusion set having an occluder formed therein in accordance with an aspect of the present invention.
Figure 6B:
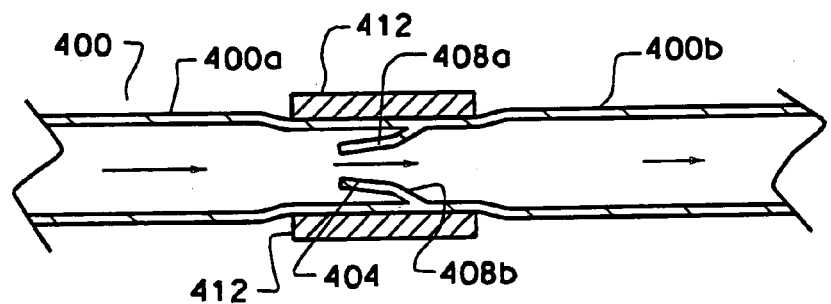
FIG. 6B shows a view similar to that shown in FIG. 6A with the occluder held in an open position.

Turning now to FIGS. 6A and 6B, there is shown yet another embodiment of the present invention. The infusion set, generally indicated at 400, has an occluder 404 disposed therein. The occluder 404 may be molded in the infusion set 400, or may be constructed separately and inserted.

The occluder 404 is formed by a first vane 408a and second vane 408b which form a duck-bill valve. The vanes 408a and 408b are disposed so that they extend proximally (i.e. upstream). As shown in FIG. 6A, the vanes 408a and 408b normally engage one other to occlude flow from a proximal portion 400a of the infusion set 400 to a distal portion 400b of the infusion set.

When pressure is applied to the tubing which forms the infusion set 400, the vanes 408a and 408b move away from each other sufficiently to allow fluid flow through the infusion set. Thus, in FIG. 6, a compression valve is formed by sliding the infusion set 400 between two walls 412 of engagement surfaces so that the vanes 408a and 408b are held apart, or by forcefully engaging the infusion set with a projection or other structure associated with a door, etc. As long as the infusion set 400 remains between the walls 412, projections, etc., fluid flow is enabled. If the portion of the infusion set 400 which contains the occluder 404 is pulled from the walls 412 or projections, the occluder will return to the closed position wherein it prevents free flow.

Preferably, the infusion set 400 and occluder 404 will be used in a housing, such as that shown in FIG. 5E. When the infusion set 400 is mounted in a channel defined by restricting sidewalls or when a cover with an aligned projection is closed, flow is enabled through the infusion set. If the infusion set 400 is pulled out of the housing, the occluder 404 will automatically close—thereby preventing free flow through the infusion set.

The various embodiments disclosed in accordance with the present invention provide a marked improvement over clamps and other types of external occluders which are commonly used to control fluid flow. These embodiments provide assurance against free flow, are generally easier to handle and are much more cost effective than the external occluders of the prior art.

In addition to being usable with housings and other fixed structures which cause the valve to open, the majority of configurations discussed above can also be manually opened by simply squeezing the infusion set adjacent the occluder to open a pathway around the occluder. The availability to manually open the occluder/infusion set is desirable, as it facilitates priming of the infusion set with the liquid being infused. Unlike many of the occluders of the prior art however, simply releasing the infusion set adjacent the occluder is all that is required to terminate flow.

Figure 7:
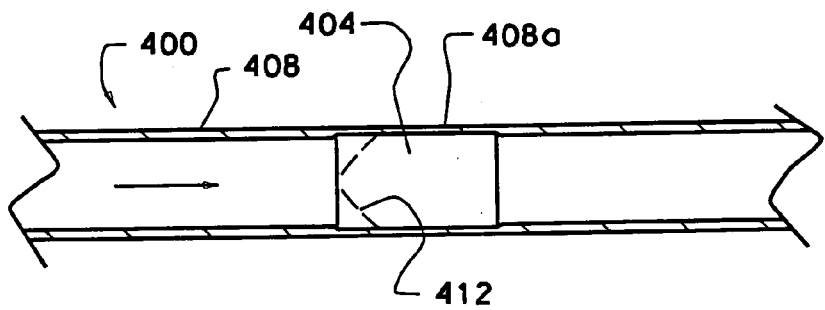
FIG. 7 shows another configuration of an occluder made in accordance with the principles of the present invention.

Turning now to FIG. 7, there is shown another configuration of an infusion set, generally indicated at 400, and an occluder, 404 made in accordance with the principles of the present invention. The infusion set 400 is formed by an elongate tube 108 made of a flexible, resilient material such as silicone rubber, latex, polyurethane, neoprene or numerous similar materials. Typically, the elongate tube has an inner diameter of approximately 0.130 inches.

The occluder 404 has an exterior diameter which is slightly larger than the interior diameter of the tube forming the infusion set 400, typically about 0.141 inches. This causes a portion 408a of the tube to stretch slightly as it passes over the occluder 404.

The occluder 404 prevents flow through the infusion set 400 based on gravity. Thus, the exact size of the occluder 404 will depend on the material used to form the infusion set 400. In a presently preferred embodiment, the infusion set 400 is formed from a tube made of silicone rubber, and the occluder 404 is formed from a plastic (e.g. acrylonitrile butyl styrene (ABS), acrylic (PMMA), polycarbonate, etc.) cylinder having an outer diameter of 0.141 inches and a length of about 0.282 inches.

Because the occluder 404 is larger than the interior diameter of the infusion set 400, solution which is under only the force of gravity will back-up behind the occluder and not pass. Once sufficient pressure is present—e.g. pressure produced by a pump—the walls of the infusion set will expand to allow fluid flow past the occluder 400 as discussed with respect to FIG. 2A, etc.

While the embodiment shown in FIG. 2A is spherical and the embodiment shown in FIG. 7 is cylindrical, those skilled in the art will appreciate that numerous other embodiments could be used. For example, the dashed line 412 illustrates an occluder which is bullet shaped. Occluders can also be egg shaped, or any other shape which provides a stop to fluid flow until a predetermined pressure threshold has been reached. It will also be appreciated that the occluder 404 need not have a consistent diameter. By having a portion of the occluder 404 extend radially a greater distance than other parts, a portion of the occluder will always engage the wall of the infusion set 400, thereby reducing the ability of the occluder to move within the infusion set.

Figure 8:
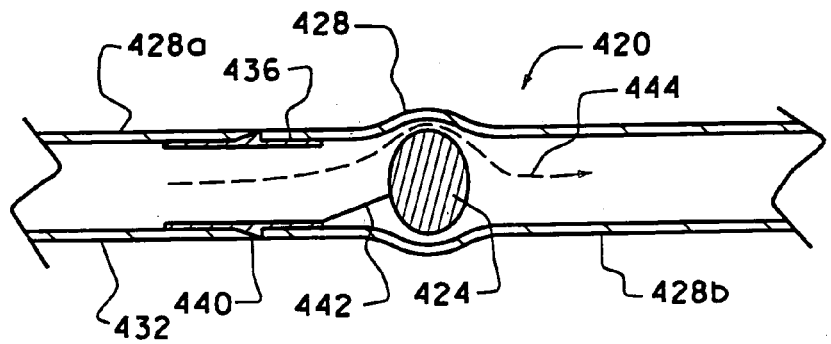
FIG. 8 shows yet another configuration of an occluder made in accordance with the principles of the present invention.

Turning now to FIG. 8, there is shown still another configuration of an infusion set 420 and occluder 424 made in accordance with the principles of the present invention. The infusion set 420 is formed from an elongate tube 428 which has a first portion 432 and a second portion 436 which are connected together by a connector 440. The occluder 424 is attached to the connector 440 by a tether 442 to prevent the occluder from advancing along the second portion 436 of the elongate tube 428.

When sufficient pressure is present in a proximal, upstream portion 428a of the elongate tube 428, the second portion 432 will expand sufficiently to allow fluid flow past the occluder 424 and into the distal, downstream portion 428b of the infusion set 420. One advantage of using the connector is that the first portion 428a of the elongate tube 428 need not be formed of a material which is resilient, or may use a material which does not expand or contract consistently. In other words, less expensive tubing materials may be used for most of the infusion set 420 without interfering with the interaction between the infusion set and the occluder 424.

While shown in FIG. 8 as being generally spherical, it should be appreciated that, in accordance with the present invention, the occluder 424 could be a variety of shapes. Additionally, a single tether 442 or a plurality of tethers could be used to hold the occluder 424 to the connector 440.

Figure 8A:
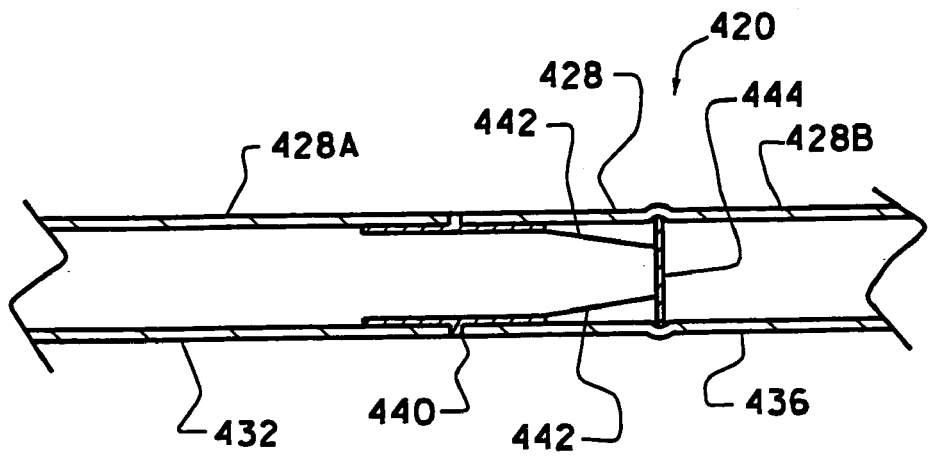
FIG. 8A shows a cross-sectional view of another configuration of an occluder in accordance with the present invention.

FIG. 8A shows a cross-sectional view of another configuration of an infusion set 420, and an occluder 444. Unlike the spherical occluder 424 of FIG. 8, the occluder 444 of FIG. 8A is disk shaped. To prevent the occluder 444 from rotating in response to fluid pressure and inadvertently opening a fluid flow path, a plurality of tethers 442 are used to secure the disk to the connector 440.

When pressure in the infusion set 420 is sufficient, the tube 428 will expand and allow fluid flow past the occluder 444. Once the pressure drops below a predetermined threshold, the tube 428 will again engage the occluder 444 and terminate flow.

Figure 8B:
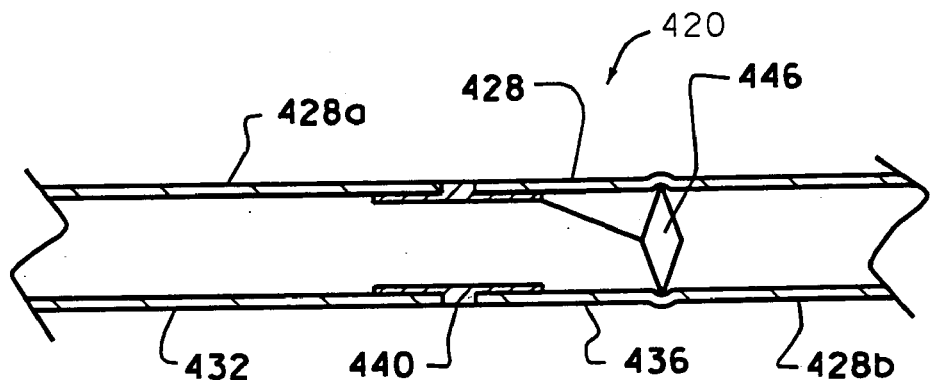
FIG. 8B shows a cross-sectional view of still yet another configuration of an occluder in accordance with the present invention.

FIG. 8B shows a cross-sectional view of still yet another configuration of an occluder, 446, made in accordance with the principles of the present invention. The infusion set 420 and related portions are the same as in FIGS. 8 and 8A and are numbered accordingly.

The connector 440 is attached by one or more tethers 442 to the occluder 446 to prevent the occluder from moving down stream. The tethers 442 can also be used to keep the occluder 446 in a desired orientation. When sufficient pressure is present, the tube 436 expands to allow fluid flow past the occluder 446.

Figure 9:
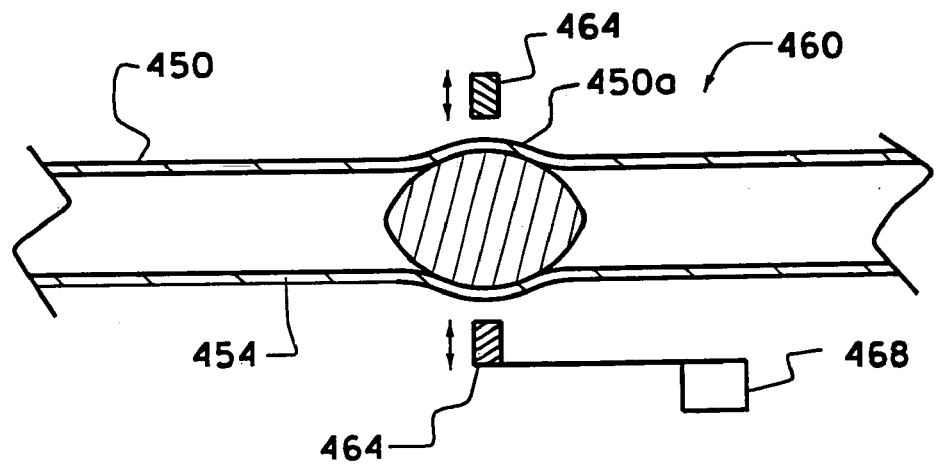
FIG. 9 shows yet another aspect of the invention wherein the occluder forms part of a liquid control valve.

FIG. 9 shows yet another aspect of the invention wherein the infusion set 450 and occluder 454 forms part of a liquid control valve, generally indicated at 460. In accordance with the embodiments discussed above, and particularly the discussion surrounding 5A through 5E, the occluder 454 normally prevents fluid flow through the infusion set. However, squeezing the infusion set on opposing sides of the infusion set sidewall 450a caused other portions of the sidewall to extend away from the occluder 454—as demonstrated in FIGS. 5C and 5D.

Disposed adjacent to the infusion set 450 and occluder 454 are a pair of engagement members 464 which are in communication with an actuator 468, such as a motor. The communication can be electronic, mechanical or pneumatic, so long as the actuator 468 is able to control movement of one or more of the engagement members 464.

When the engagement members are actuated, they apply an inward force to the infusion set 450 at the location of the occluder 454 to open a passage way around the occluder and thereby enable fluid flow through the infusion set. When the engagement members 464 are adjusted to no longer apply sufficient force to the infusion set 450, the infusion set again surrounds the occluder 454 and prevents fluid flow.

By selectively actuating the engagement members 464, the infusion set 450 and occluder 454, a valve is formed for controlling fluid flow. By applying a pressure sensor or other type of sensor, the valve can be used to regulate flow and flow through the valve can be determined.

Figure 10:
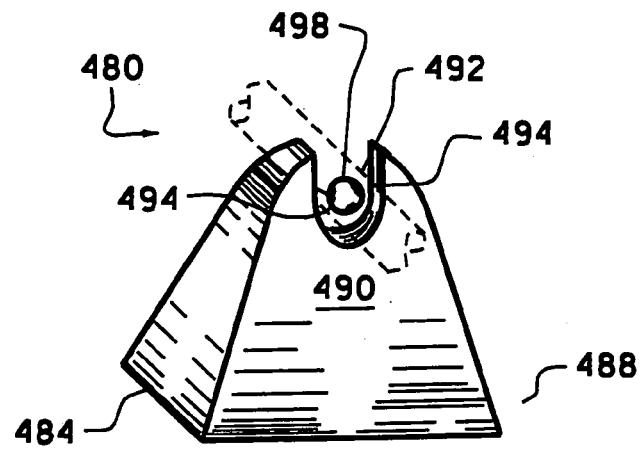
FIG. 10 shows a perspective view of a clip for retrofitting existing pumps of use with an occluder of the present invention.

Turning now to FIG. 10, there is shown a perspective view of a clip, generally indicated at 480, for opening flow between an occluder and infusion set. Those skilled in the art will appreciate that there are a number of enteral and parenteral pumps in the market which use various types of occluders which suffer from the problems identified in the background section. To eliminate these concerns, the clip 480 is configured for retrofitting an existing pump for use with an occluder/infusion set made in accordance with the principles of the present invention. (Of course, with some existing pumps, the occluder and infusion set may be configured to nest in the pump in such a manner that retrofitting is not necessary.)

The clip 480 includes a base 484 which is provided for attachment to the housing of a conventional fluid pump. Typically, the base 484 will have an adhesive disposed thereon. If desired, the adhesive may be selected from removable adhesives, such as those known to those skilled in the art, so that the clip 480 can be removed from the pump when an infusion set containing an occluder (such as that represented by the dashed lines 488) is not being used with the pump.

Extending from the base 484 is a fitting 490 having channel 492 formed therein. The channel 492 is preferably formed with an open end and extends into the clip 480. As the infusion set, represented in shadow at 488, is inserted into the channel 492, walls 494 defining the channel compress the infusion set 488 against the occluder (shown as dashed lines 498) to open a pair of flow channels between the occluder and the infusion set as shown in FIGS. 5A through 5D.

As long as the infusion set 488 and occluder 498 remain securely held between the walls 494 defining the channel 492, fluid flow is enabled between the occluder and the infusion set. If the infusion set 488 is pulled from the channel 492 or is never properly placed in the channel, flow through the infusion set is prevented. Thus, the risk of free flow developing within the system is significantly reduced. Of course, the risk of free flow can virtually be eliminated by placing the clip 480 on the pump in such a manner that the infusion set 488 must be properly loaded in the pump in order to fit within the channel 492.

Figure 11:
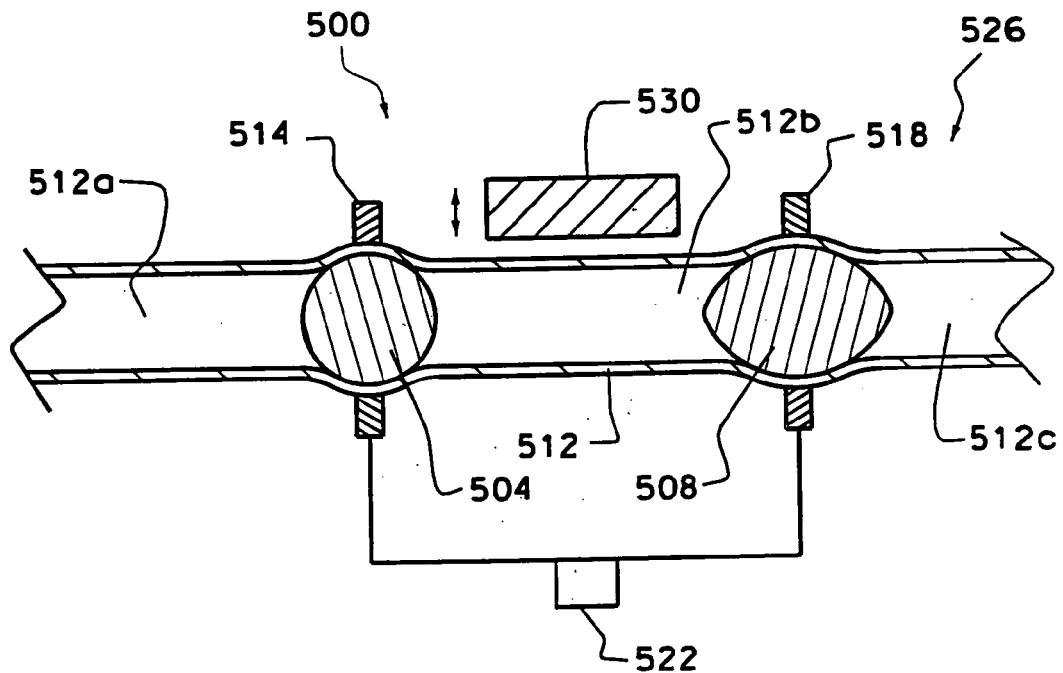
FIG. 11 shows a side cross-sectional view of a pair of occluders and infusion line which form a pair of valves, and a force applicator to form a linear peristaltic pump.

FIG. 11 shows a side cross-sectional view of yet another embodiment of the present invention which forms an in-line pump, generally indicated at 500. As shown in FIG. 11, a pair of occluders 504 and 508 are disposed in an infusion line 512. Each of the occluders 504 and 508 is disposed adjacent an actuator 514 and 518, respectively. The actuators 514 and 518 are configured to selectively apply pressure to the infusion line 512 to selectively open flow channels between the infusion line and the occluder 504 or 508 with which each is associated.

In use, liquid in the infusion line 512 will be held in a proximal portion 512a which is upstream from the first occluder 504. The first occluder 504 prevents the liquid from flowing down stream until a drive mechanism 522 causes the first actuator 514 to apply force to the infusion line 512 adjacent the first occluder. Applying force to the infusion line 512 causes a channel to open between the first occluder 504 and the infusion line, thereby allowing fluid flow into a middle portion 512b of the infusion line.

Once the middle portion 512b of the infusion line 512 has had adequate time to fill with liquid, the actuator 514 is adjusted so that it no longer applies sufficient force to the infusion line to enable fluid flow around the occluder 504. The liquid in the middle portion 512b of the infusion line 512 is then isolated from the liquid in the proximal portion 512a.

The liquid in the middle portion 512b of the infusion line 512 is prevented from flowing distally or downstream by the second occluder 508 which defines the distal end of the middle portion. However, once the drive mechanism 522 is actuated to move the actuator 518 into forceful contact with the infusion line 512 adjacent the occluder 508, one or more channels are formed between the occluder and the infusion line. The channel(s) opened by the actuator 518 squeezing the infusion line 512 form a flow path allowing the liquid contained in the middle portion 512b to flow into a distal, downstream portion 512c. Since no occluder or other stop is typically disposed distally from the second occluder 508, the liquid flowing into the distal portion 512c is delivered to the patient.

By selectively controlling the application of force by the first actuator 514 on the infusion line 512 and first occluder 504 and the application of force by the second actuator on the infusion line and second occluder 508, a valve, generally indicated at 526, is formed which permits a predetermined amount of flow to pass with each series of actuations.

In a more preferred embodiment, the valve also includes a force applicator 530, such as a plunger, roller or similar device, disposed in communication with the middle portion 512b of the infusion line 512. The force applicator 530 applies a compressive force to the middle portion 512b of the infusion line 512 to force the liquid contained in the middle portion 512b to flow into the distal portion 512c of the infusion line 512 and on to the patient. The force applicator 530 ensures that liquid will not simply remain in the middle portion 512b when the second actuator 518 causes a flow path to be formed between the second occluder 508 and the infusion line 512.

While applying a compressive force to the middle portion 512b of the infusion line 512 helps to force the liquid in the middle portion to flow downstream, it also serves to assist flow into the middle portion. Once a compressive force is no longer applied to the middle portion 512b, the resilient material forming the infusion line will attempt to return to its original, tubular configuration. By closing the flow path between the second occluder 508 and the infusion line 512 before releasing force applicator 530, a vacuum is formed within the middle portion 512b. Once the actuator 514 opens a flow path between the first occluder 504 and the infusion line 512, the vacuum in the middle portion 512b will draw liquid into the middle portion 512b as the infusion line returns to its original configuration.

In each cycle of the valve 526, the first actuator 514 will open a flow channel between the first occluder 504 and the infusion line 512 to fill the middle portion 512b with liquid. The first actuator 514 will then allow the flow channel to close. The second actuator 518 will then open a flow channel between the second actuator 508 and the infusion line 512 and the force applicator 530 will apply pressure to the infusion line forming the middle portion 512b so that the liquid in the middle portion will flow into the distal portion 512c and to the patient. The second actuator 518 will then allow the flow channel between the second occluder 508 and the infusion line 512 to close. The process will then be repeated.

By controlling the interior diameter of the infusion line 512, the distance between the first occluder 504 and the second occluder 508, and the movement/size of the force applicator 530, one can obtain a predetermined amount of liquid flow with each cycling of the valve 526. By controlling the number of cycles in a predetermined period of time, the operator is able to provide a highly accurate rate of flow for the solution passing through the valve 526. Furthermore, because a rotor is not needed to control flow rate, the valve 526 can be used to make an in-line peristaltic pump which is significantly thinner than conventional peristaltic pumps while maintaining the same accuracy.

While FIG. 11 shows two actuators, those skilled in the art will understand, in light of the present invention, that one of the occluders could be configured to allow fluid flow responsive to force if configured properly to prevent back flow. This could be achieved, for example, by controlling the size of the occluders.

Figure 12A:
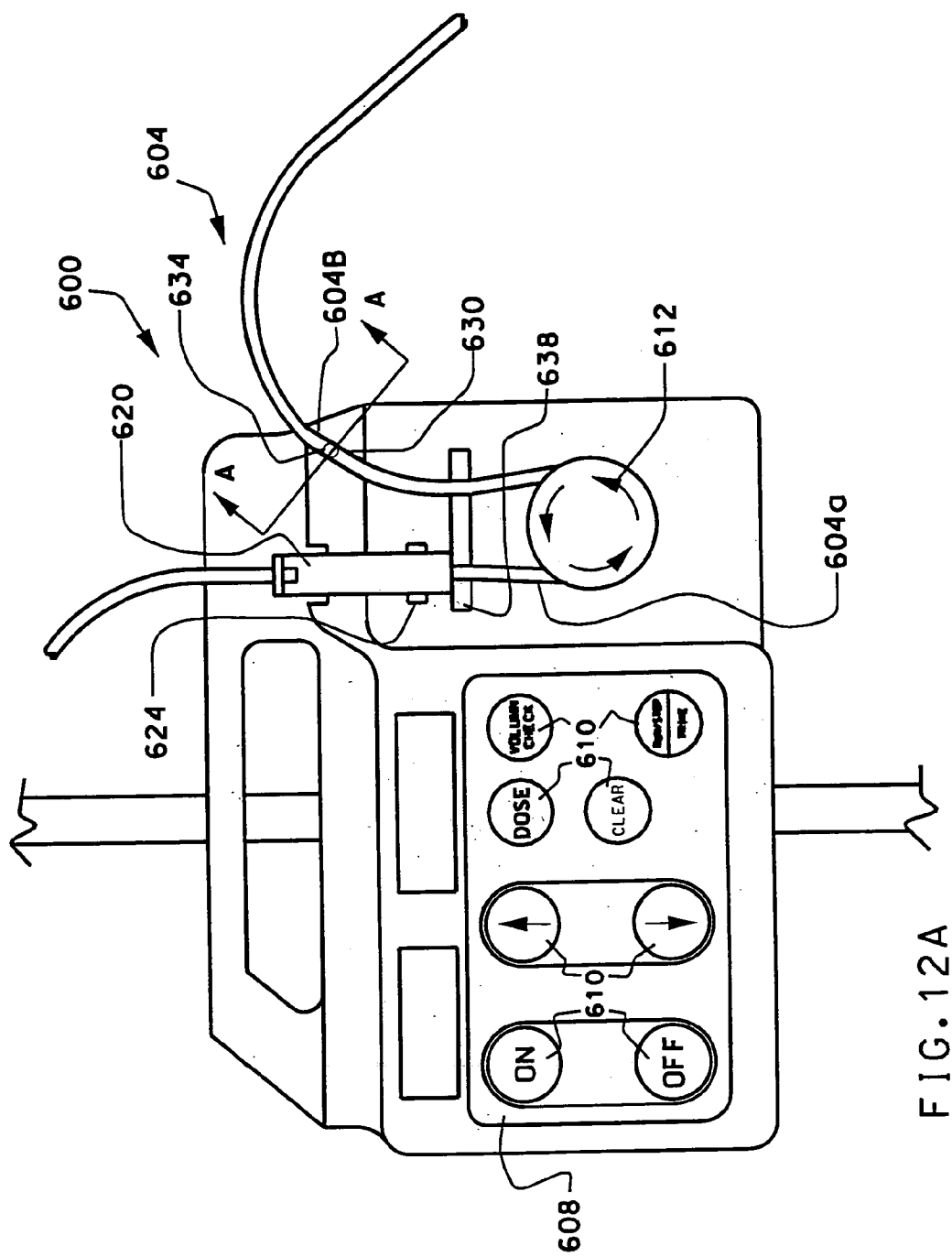
FIG. 12A shows a front view of an enteral feeding pump of the prior art with an occluder in accordance with the present invention disposed therein.

Turning now to FIG. 12A, there is shown a perspective view of a pump, generally indicated at 600, which is designed to control fluid flow through an infusion set, generally indicated at 604, and into the patient. The pump 600 includes a control panel 608 which has a plurality of buttons 610 or other devices for controlling the actuation of the pump. The pump 600 operates to deliver a predetermined dose of enteral feeding solution to a patient by rotation of a rotor 612.

The infusion set 604 is mounted on the pump so that a resilient portion 604*a* of the infusion set wraps around the rotor 612. Each rotation or partial rotation of the rotor 612 causes a predetermined amount of enteral feeding solution to be advanced through the infusion set 604 and delivered to the patient.

In order to assure that the rotor 604 is providing the proper amount of enteral feeding solution, a drip chamber 620 is formed along the infusion set. An optical sensor 624 is disposed in the enteral feeding pump 600 and monitors the drip rate of the solution in the drip chamber 624. The drip rate of the solution is used to calculate an actual delivery rate of the solution.

As with the prior art, a portion 604*b* of the infusion set disposed distally from the rotor 612 is nested in a channel 630 in the pump housing 600. In accordance with the present invention, the portion 604*b* has an occluder 634 disposed therein. While the prior art simply used the channel 630 to hold the infusion set 604 in contact with the rotors, the inclusion of an occluder 634 provides an improved measure of safety.

In the prior art, if either the portion 604*b* of the infusion set 604 was not properly positioned in the channel 630, a free flow condition could develop in which fluid flow through the infusion set would be unchecked by the rotor 612. In the present invention, flow through the infusion set 604 is not permitted until the portion 604*b* with the occluder 634 is nested in the channel 630. If the portion 604*b* of the infusion set 604 is not properly placed in the channel 630 or is pulled from the channel, the occluder 630 will prevent free flow through the infusion set.

Figure 12B:
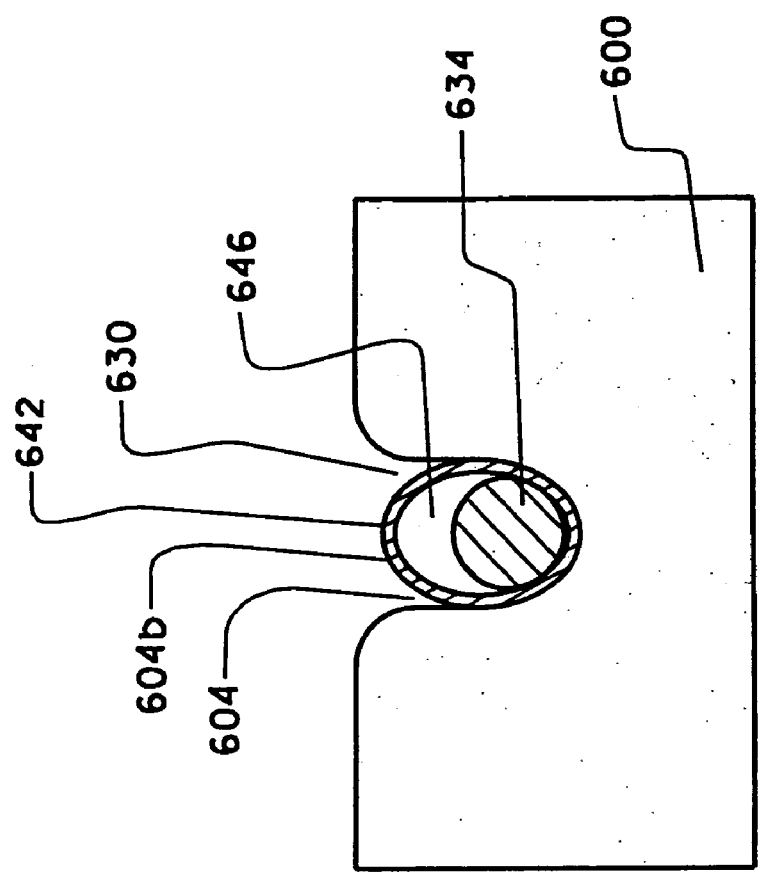
FIG. 12B shows a close-up, cross-sectional view of the occluder, infusion set and a portion of the pump to demonstrate opening of a fluid flow pathway around the occluder.

FIG. 12B shows a close-up, cross-sectional view of the portion of the pump 600 having the channel 630 formed therein taken along the line A—A. The channel 630 receives the infusion set 604 in such a manner that it compresses the tube 642 against the occluder 634. This causes another portion of the tube 642 to extend away from the occlude 634 and thereby open a fluid flow path between the inner wall of the tube and the occluder.

As shown in FIG. 5D, compressing opposing sides of the infusion set can open fluid flow channels both above and below the occluder. In FIG. 12B, the tube 642 of the infusion set 604 is pressed against one half of the occluder 634, thereby forming a single fluid flow channel 646 on the opposing side. If the portion 604*b* of the infusion set 604 containing the occluder 634 is pulled from the channel 630, the infusion set will engage the occluder and prevent fluid flow.

Figure 13A:
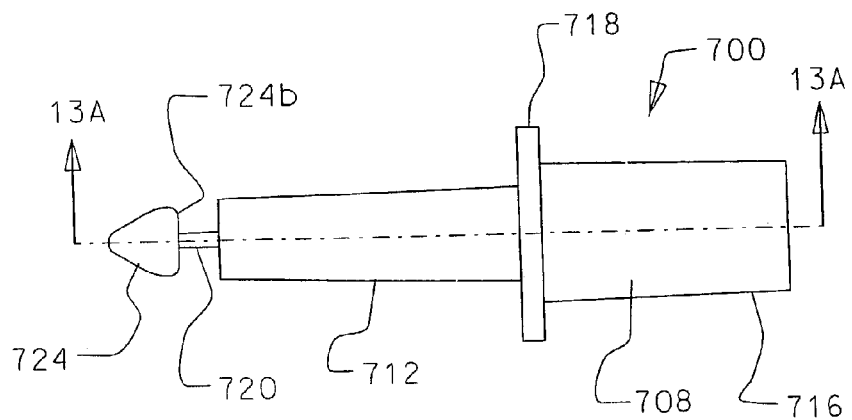
FIG. 13A shows a side view of an alternate embodiment of an occluder made in accordance with the principles of the present invention.

Turning now to FIG. 13A, there is shown a connector having still another embodiment of the present invention. The connector 700 is formed by an adaptor body 708 which is used to connect to pieces of tubing together. Most commonly, the adaptor body 708 is used to connect a silicone tube segment which engaged the pump rotor, to the remaining tubing of an infusion set (not shown.) Such connectors 700 are used on a variety of infusion sets currently in use.

The adaptor body 708 is formed by a proximal section 712, a distal section 716, and an annular flange 718 which limits the advancement of tubing the proximal and/or distal sections of the adaptor body. The proximal section 712 usually engages the silicone tubing, while the distal section 716 engages the remaining tubing of the infusion set.

An arm 720 forming a tether/spacer extends proximally from the proximal portion 712, and holds an occluder 724 a spaced distance from the rest of the adaptor 708. Unlike the prior embodiments discussed above, the occluder 724 is generally tear drop shaped when the adaptor 708 is standing on end. As shown in FIG. 13*a*, the distal end 724*a* of the occluder 724 may be squared off. However, it may also be rounded or otherwise contoured. In light of the embodiments discussed above, those skilled in the art will appreciate that a spherical, diamond shape or other shaped occluder could also be used.

Unlike the tether arrangements discussed in previous embodiments, the arm 720 holds the occluder 724 generally rigidly and proximally from the adaptor. In the event the arm 720 were to be broken by improper bending of the infusion set in which the adaptor body 708 is mounted, the occluder 724 would not be able to move down stream in the infusion set. To the contrary, adaptor body 708 would prevent distal movement and the position of the arm and the shape of the occluder 724 would prevent the occluder from completely blocking flow through the tube so long as the designated pressures are being used to properly expand the tube.

Figure 13B:
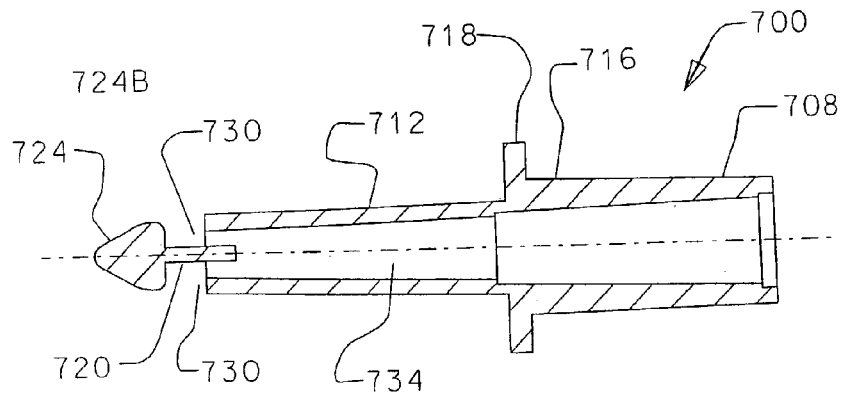
FIG. 13B shows a cross-sectional view of the occluder embodiment of FIG. 13A taken along the line 13A—13A.
Figure 13C:
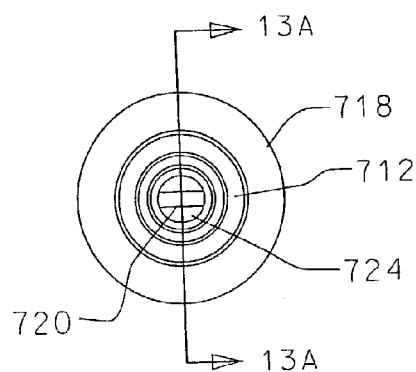
FIG. 13C shows an end view of the occluder of FIGS. 13A and 13B.

Turning now to FIG. 13B, there is shown a cross-sectional view of the connector 700 shown in FIG. 13A. This view demonstrates the two flow channels 730 which are formed on either side of the arm 720. The two flow channels 730 are configured to allow fluid which had flowed passed the occluder 724 to enter the hollow channel 734 of the adaptor body 708 and to flow downstream from the occluder. An end view of the connector 700 is shown in FIG. 13C.

The opening in the proximal end of the proximal section 712 is preferably about 0.098 inches in diameter and is bisected by the arm 720 which is about 0.03 inches thick. The occluder 724 is preferably spaced about 0.085 inches from the proximal section 712, and is provided with a radius of curvature of 0.025 inches on the front end. The rounded portion of the distal end is typically about 0.03 inches long.

The spacing of the occluder 724 from the proximal section 712 and the size of the flow channels 730 are sufficient to allow fluid to flow readily through the connector 700 if the pressure is above about 5 psi. If the pressures are below about 5 psi, the occluder 724 will prevent flow of the fluid through the connector 700.

Having the occluder 724 be formed as part of the connector 700 has several distinct advantages. First, it has been found that the occluder 724 can be formed by molds substantially the same as the molds currently used for such parts. Thus, rather than having to engineer an entirely new product, infusion set manufacturers can readily adapt their molds to add the occluder 724. The cost of adapting the mold is almost negligible. Additionally, the amount of additional plastic used to form the occluder raises the cost of producing the connector 700 by a mere fraction of a cent. This is in contrast to presently available pinch clip occluders and clamps which can cost ten to twenty cents and constitute more than ten percent of the cost of the infusion set. Thus, for almost no cost, the infusion set can be provided with a highly reliable anti-free flow device.

Figure 13D:
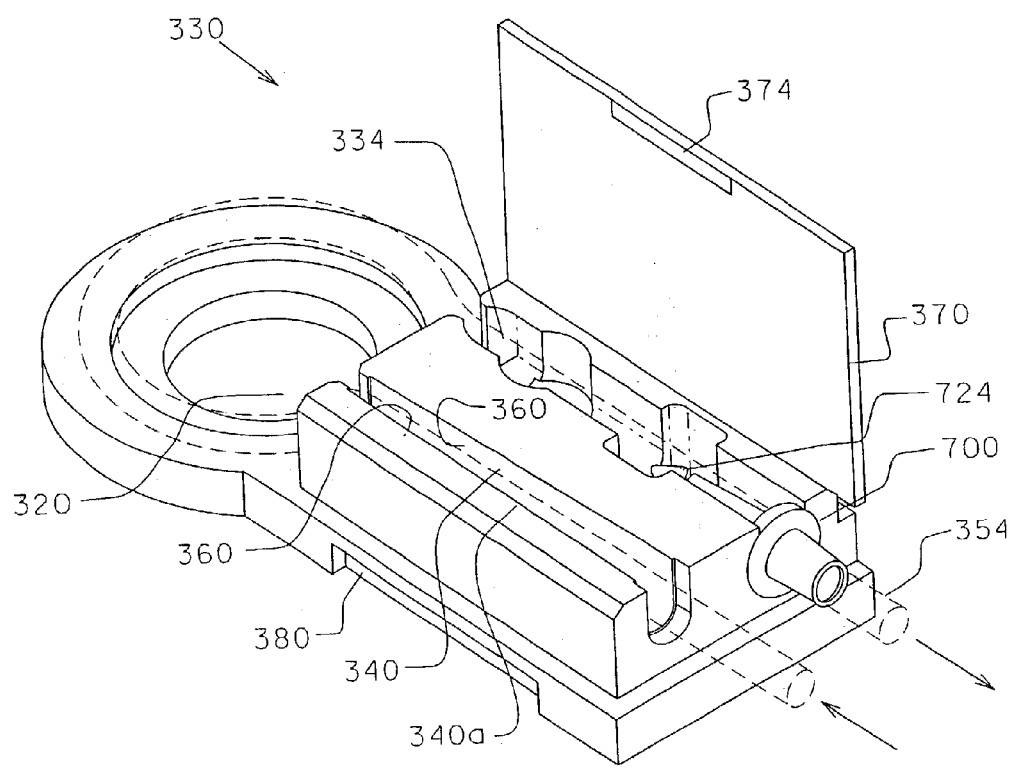
FIG. 13D shows a top view of an enteral feeding pump having an infusion set disposed therein, with an occluder positioned in the infusion set to prevent free-flow therethrough in accordance with the present invention.
Figure 13E:
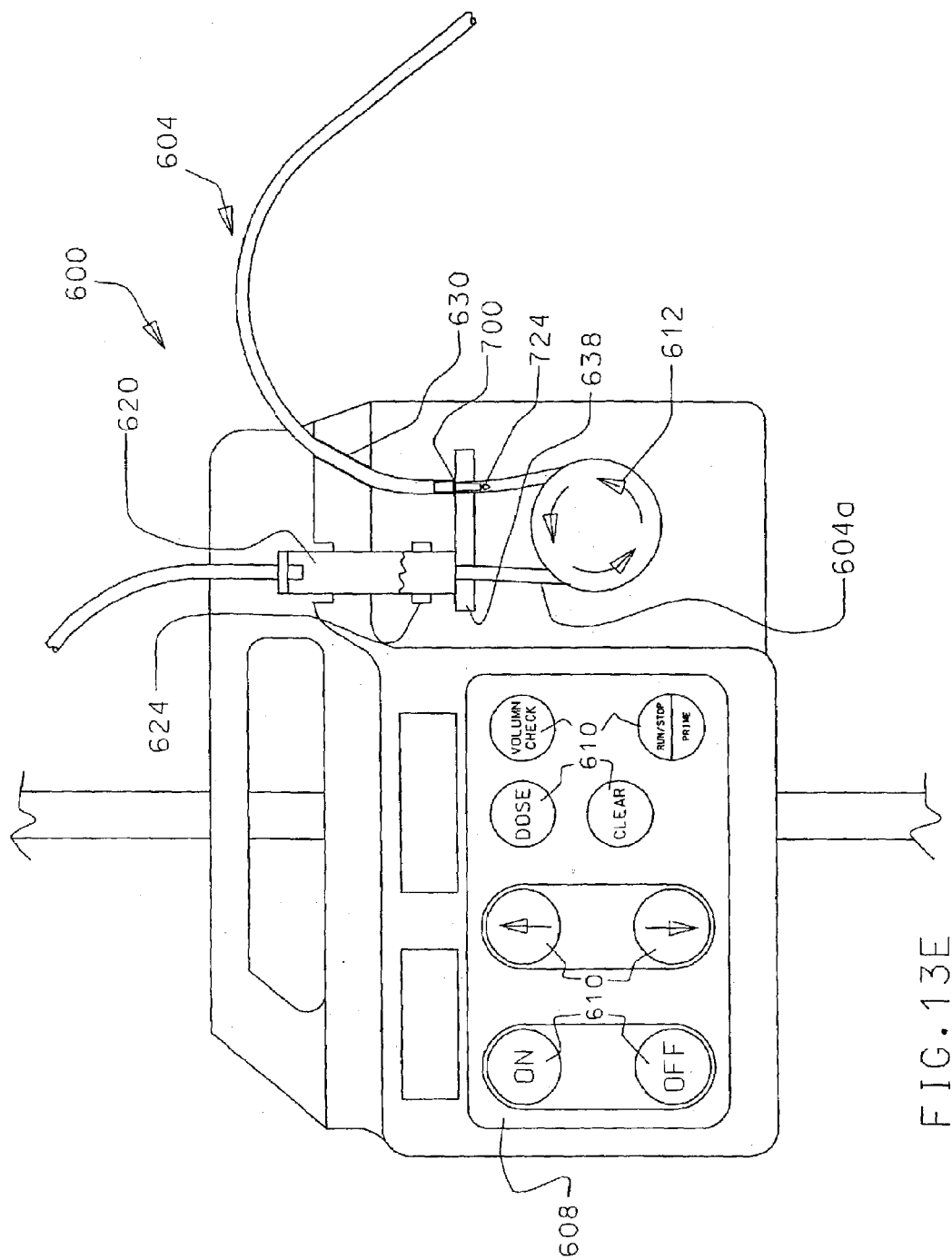
FIG. 13E shows a front view of another available enteral feeding pump having an infusion set disposed therein, with an occluder positioned in the infusion set to prevent free-flow therethrough in accordance with the present invention.

FIGS. 13D and 13E shown the pumps discussed in FIGS. 5E and 12A, respectively. To avoid excessive repetition, the pumps are portions of the pumps which are similar to those drawings are labeled according.

As shown in FIGS. 13D and 13E, the connector 700 is preferably mounted to the infusion pump downstream from the pump rotor 750 (FIG. 13D) and 760 (FIG. 13E). As the pump rotor 750/760 rotates, it will create sufficient pressure to cause the fluid being pumped to pass around the occluder 724 and into the channel 734 (FIG. 13B) in the connector 700. The fluid is then free to flow down stream.

The connector 700 is highly advantageous because it can be used on most infusion pumps without the need for retrofitting or otherwise modifying the infusion set. It eliminates the need to recess an occluder as shown at numeral 630/634 in the pump shown in FIG. 12A, and eliminates the need for modified channels 340/340a or a projection 384 as discussed with respect to FIG. 5A. When mounted in the infusion set, the connector 700 appears substantially the same as the conventional connector and the patient may not even know it is being used unless told. However, the advantages of conventional pinch clip occluders, etc., are achieved without the disadvantages.

Figure 14:
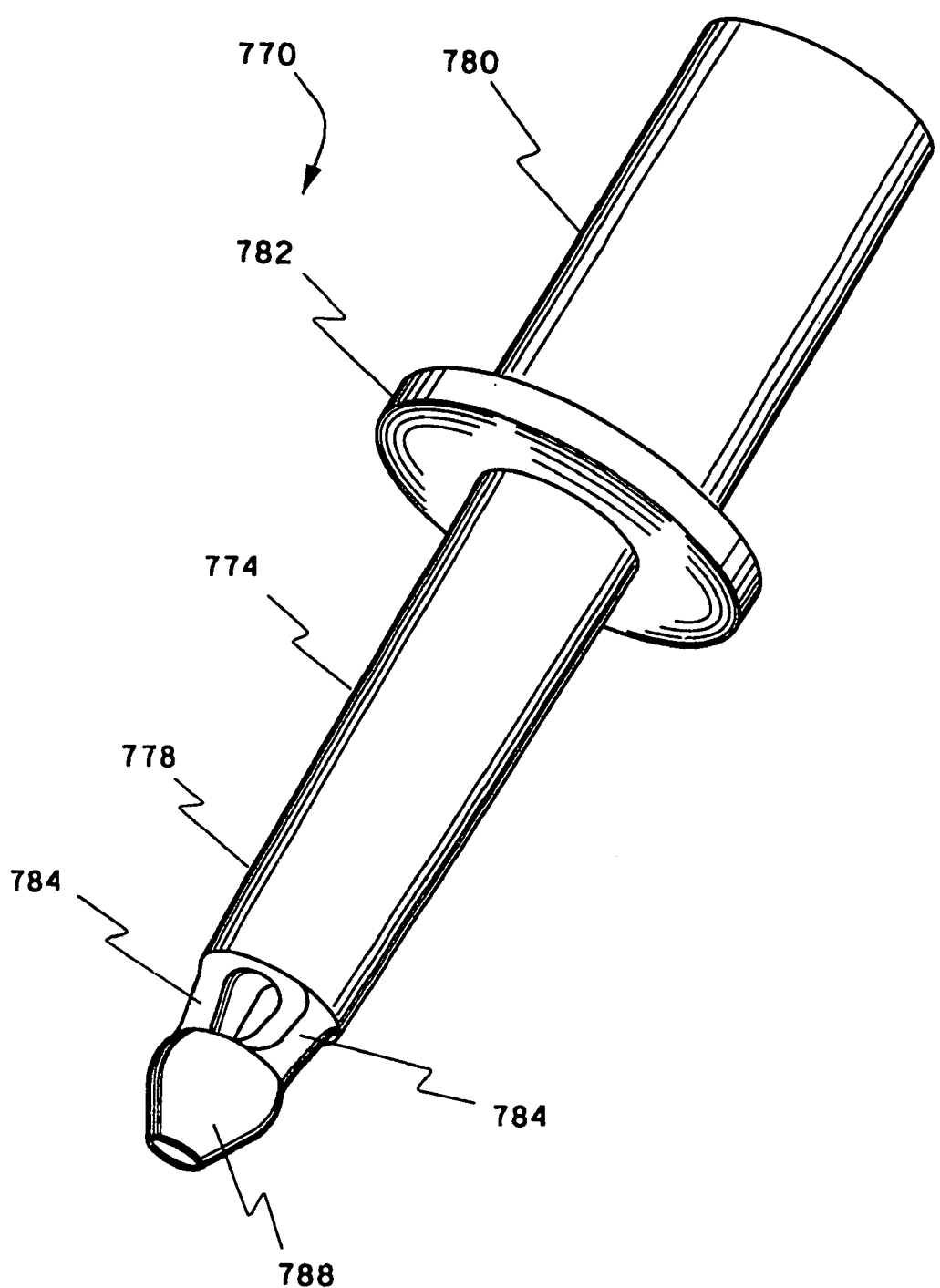
FIG. 14 shows a perspective view of an alternate embodiment of an occluder made in accordance with the principles of the present invention.
Figure 14A:
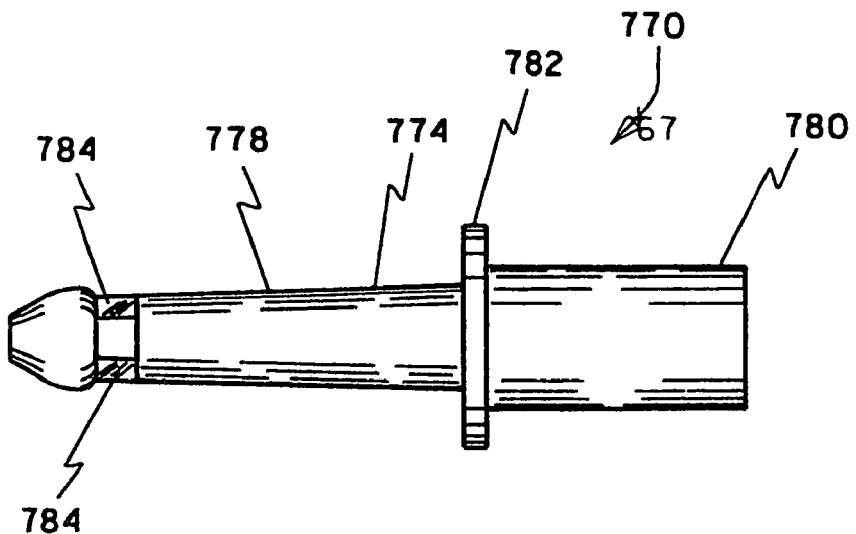
FIG. 14A shows a side view of the occluder of FIG. 14.
Figure 14B:
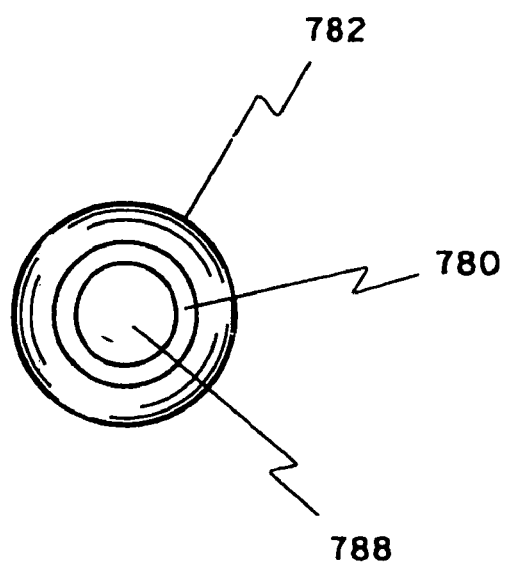
FIG. 14B an end view of the occluder of FIG. 14.

Turning now to FIGS. 14 to 14B, there is shown an alternate embodiment of a connector or adaptor, generally indicated at 770, made in accordance with the principles of the present invention. The connector 770 is typically formed by an adaptor body 774 which is used to connect two pieces of tubing together. However, it will be appreciated in light of the present disclosure that such a structure is not required. Most commonly, the adaptor body 774 is used to connect a silicone tube segment which engaged the pump rotor, to the remaining tubing of an infusion set (not shown.)

The adaptor body 774 is formed by a proximal section 778, a distal section 780, and an annular flange 782 which limits the advancement of tubing the proximal and/or distal sections of the adaptor body. The proximal section 778 usually engages the silicone tubing, while the distal section 780 engages the remaining tubing of the infusion set.

Rather that being connected by a tether/spacer as shown in FIGS. 13A and 13B which extends into the interior of the proximal section 778, the tether/spacer 784 forms a pair of arms which connect the occluder or stop 788 to the adaptor body 774. It has been found that using a pair of arms as the tether/spacer 784 decreases the risk of an obstruction preventing flow through the adaptor body 774. Because the arms 784 are not disposed in alignment with a hollow channel 790 in the adaptor body, greater unobstructed area is available for moving enteral feeding solution through the adaptor. This is especially true if the feeding solution is somewhat viscous. The arms forming the tether/spacer 784 are also advantageous in that they securely hold the occluder or stop away from the adaptor body 774 in a generally rigid manner and reduce the risk that the stop or occluder 788 will be broken off from the adaptor body.

By matching the occluder 788 with an appropriately sized infusion set tube, a valve can be formed which will open the valve to the flow of liquid once a predetermined pressure threshold has been reached, but generally prevent free flow when the pressure falls below the predetermined threshold. Those skilled in the art will appreciate that the pressure threshold at which the seal between the tubing and the occluder 788 will crack is a function of the relative sizes of both, along with the elasticity of the tubing.

Figure 15:
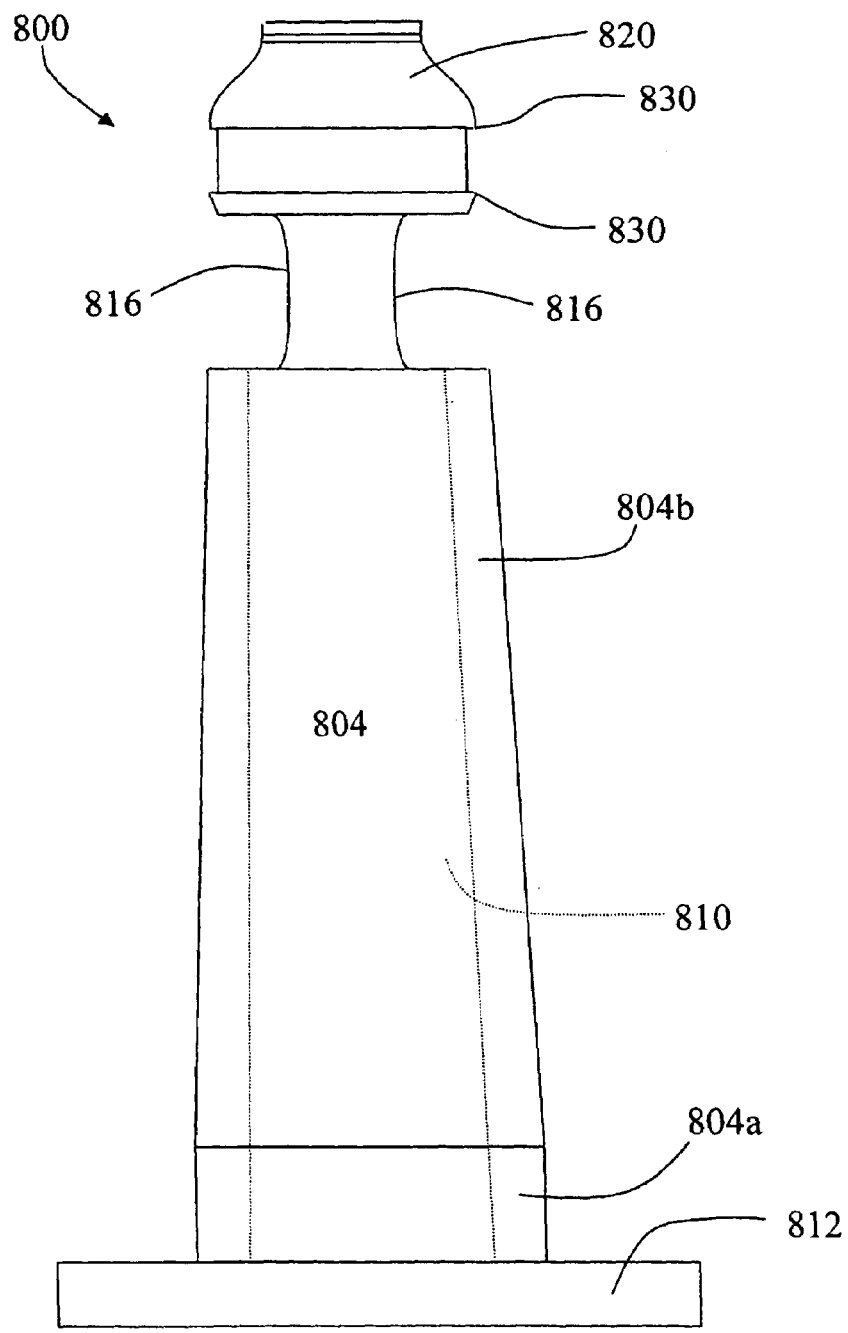
FIG. 15 shows a top view of yet another embodiment of an occluder made in accordance with the principles of the present invention.
Figure 15A:
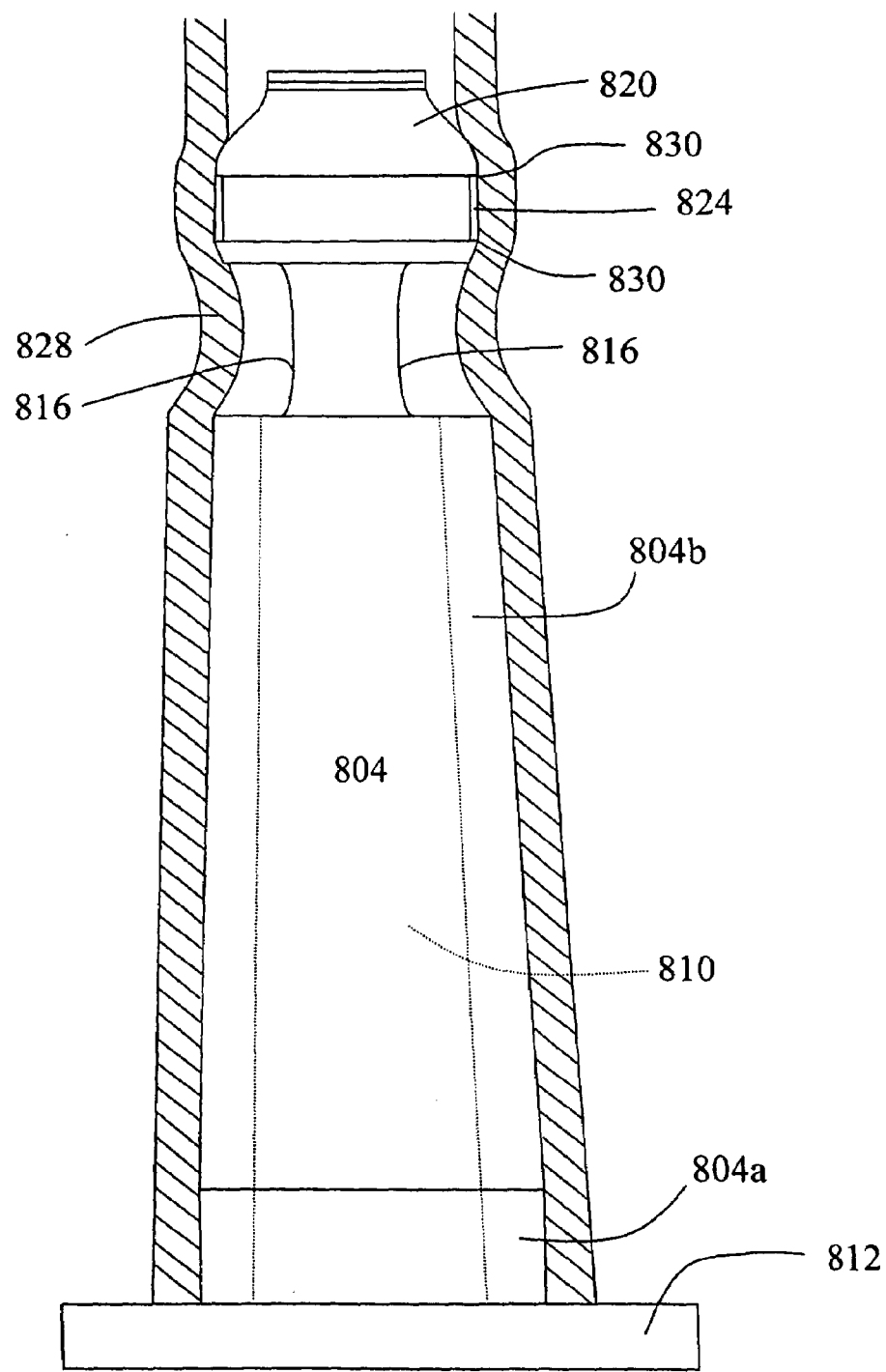
FIG. 15A and FIG. 15H show cross-sectional views of a portion of an infusion set with the occluder of FIG. 15 disposed therein.

FIG. 15 shows a top view of yet another embodiment of an in-line occluder, generally indicated at 800, made in accordance with the principles of the present invention. FIG. 15A shows the occluder disposed in a tube 808 of an infusion set. The configuration is referred to generally as an in-line occluder simply to illustrate that the configurations shown herein can be used in conjunction with two tubes as an adaptor, or can be inserted into a single tube. It is presently preferred that the in-line occluder be used as an adaptor for connecting tubing segments. However, it should be appreciated that such is not a requirement and the in-line occluder 800 can be disposed completely within a single tube.

The in-line occluder 800 includes a body 804 configured to nest in a tube of an infusion set. To this end, the body 804 may include a generally cylindrical distal portion 804a and a tapered proximal portion 804b. The tapered portion 804b assists in the insertion of the body into the tube.

Attached to the distal portion 804a is a flange 812 which can be used for securing the position of the occluder 800 in an enteral feeding pump. If the body 804 were desired to be disposed completely in a tube, the flange 812 could be omitted.

Attached to the proximal portion 804a by one or more arms 816 is an occluder or stop 820. As with the previous embodiment, it is preferred to have two arms which connect the proximal portion or stop without extending into a hollow portion or channel of the body 810 to thereby minimize interference with fluid flow.

One concern which has been raised with having a broadly rounded portion of the occluder or stop 820 which engages the tubing of an infusion set is that the friction between the stop 820 and the tubing can prevent the tubing from resealing against the stop after it has been activated to form a flow channel around the stop. If a seal is not maintained, a free flow condition could result.

In accordance with one aspect of the present invention, it has been found that an improved seal can be achieved by not using broadly rounded stops. More specifically, it has been found that providing the stop 820 with an annular detent or channel 824 in a sealing portion 828 provides an improved seal and virtually eliminates the risk of leakage. Furthermore, it is preferred that the channel 824 is defined by relatively sharp edges 830. Thus, for example, the edges can have a radius of about 0.003 inches, plus or minus 0.002. The sloped walls at the proximal portion of the stop 820 are preferably disposed at an angle between about 60 and 70 degrees, and the back of the stop is preferably beveled at about 120 degrees. With the overall width being about 0.155 inches, the stop 820 forms a highly effective occluder in an infusion set tube.

Ironically, the relatively sharp edges and the channel 824 improve sealing by decreasing the amount of surface area over which the tubing and the stop 820 engage each other. The reduction in surface area minimizes the amount of friction for the tubing 808 to move from an open position back into a closed position once it is no longer being pinched or once the pressure in the tubing drops below the predetermined threshold. Effectively, the channel 824 allows the tubing to collapse more and to thereby form a better seal.

The channel 824 need not be large. To the contrary, a channel which is $^{30-40}/_{1000}$ ths of an inch deep and $^{30}/_{1000}$ ths to about $^{50}/_{1000}$ ths work significantly better than a prior art configuration with a broadly rounded stop of course, the remainder of the stop 820 can be any desired shape. Thus, as shown in FIGS. 15 and 15A, the stop 820 has a blunted proximal end.

Figure 15B:
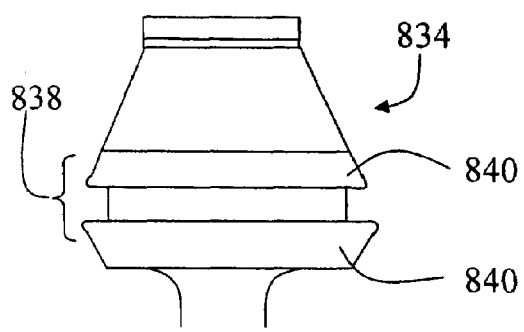
FIG. 15B shows a top view of a stop of an occluder showing an alternate configuration for the stop relative to that shown in FIG. 15.

Turning now to FIG. 15B, there is shown an alternate embodiment of an occluder or stop 834. The stop 834 will typically be attached to a body, which will not be discussed here. The stop includes a sealing portion 838 which is configured to seal against the tubing of an infusion set, etc. The sealing portion 838 in FIG. 15B is different than that shown in FIGS. 15 and 15A in that it provides a pair of bevels 840 in the sealing portion 838 of the stop. The bevels 840 help to form seals with an infusion tube by reducing friction and minimizing engaged surface area.

Figure 15C:
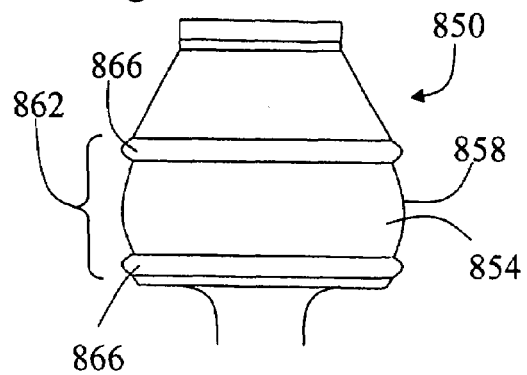
FIG. 15C shows a top view of an alternate embodiment of an occluder stop.

FIG. 15C shows an alternate embodiment of an occluder, generally indicated at 850, made in accordance with the principles of the present invention. The occluder 850 includes a stop 854 The stop 854 includes broadly rounded sides 858 disposed along the sealing portion 862. To facilitate sealing between the stop 854 and the tubing, one or more ribs 866 are disposed on the stop 854. The ribs 866 extend outwardly so that engagement of the ribs and the tubing of the infusion set encourages the tubing to flatten out in the sealing area 862 and form a seal with the ribs. Again, the reduced surface area of the ribs 866 which is engaged by the tubing helps to minimize friction and allow the tubing to quickly reseal in the event that it is not being pinched open or forced open due to the pressure in the tubing.

Figure 15D:
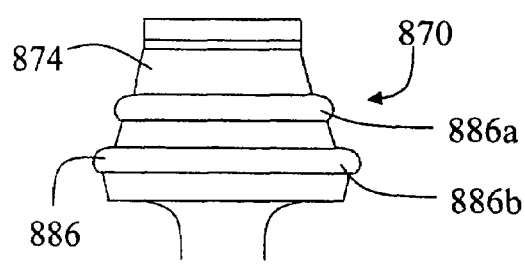
FIG. 15D shows a top view of another embodiment of an occluder stop.

Turning now to FIG. 15D, there is shown a fragmented view of an occluder, generally indicated at 870, which forms a stop 874. Disposed on the stop 874 in the sealing area 882 are a pair of annular ribs or rings 886. Unlike the ribs 866 shown in FIG. 15C, the ribs 886 of FIG. 15D do not extend radially outwardly to the same extent. Thus, a proximal rib 886a does not extend out as far as the distal rib 886b. Those skilled in the art will appreciate that with the ribs present, the underlying shape of the stop 870 becomes less important, as the ribs help form the sealing with the tubing while minimizing friction.

Figure 15E:
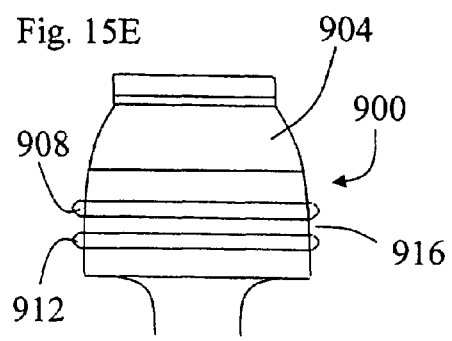
FIG. 15E shows a top view of yet another occluder stop made in accordance with the principles of the present invention.

FIG. 15E shows still another occluder, generally indicated at 900 which includes a stop 904 having a first rib or ring 908 and a second ring 912 in the sealing area 916. While the ribs 908 and 912 extend generally radially to the same extent, they are different than the embodiment shown in FIG. 15C in that they are positioned close together. It will be appreciated in light of the present disclosure that the most desirable distance between ribs will be a function both of the curvature, if any of the exterior of the ribs, along with the relative elasticity, flexibility and friction of the tubing.

Figure 15F:
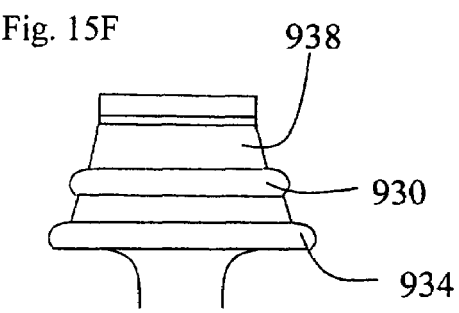
FIG. 15F shows a top view of still another stop of an occluder showing an alternate configuration for the stop relative to that shown in FIGS. 15 through 15E.

While the ribs 908 and 912 are relatively thin, broader ribs, such as ribs 930 and 934 used on the stop 938 shown in FIG. 15F. Thus, it will be appreciated that numerous different stop formations can be used to more securely effectuate sealing of the tubing to prevent free flow.

Figure 15G:
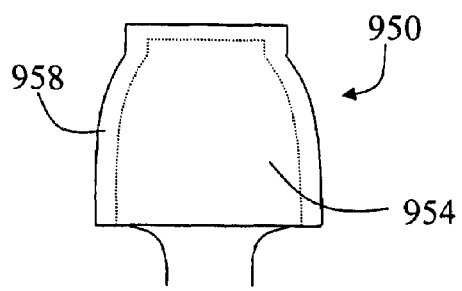
FIG. 15G shows a top view of still another stop of an occluder in accordance with the principles of the present invention.
Figure 15H:
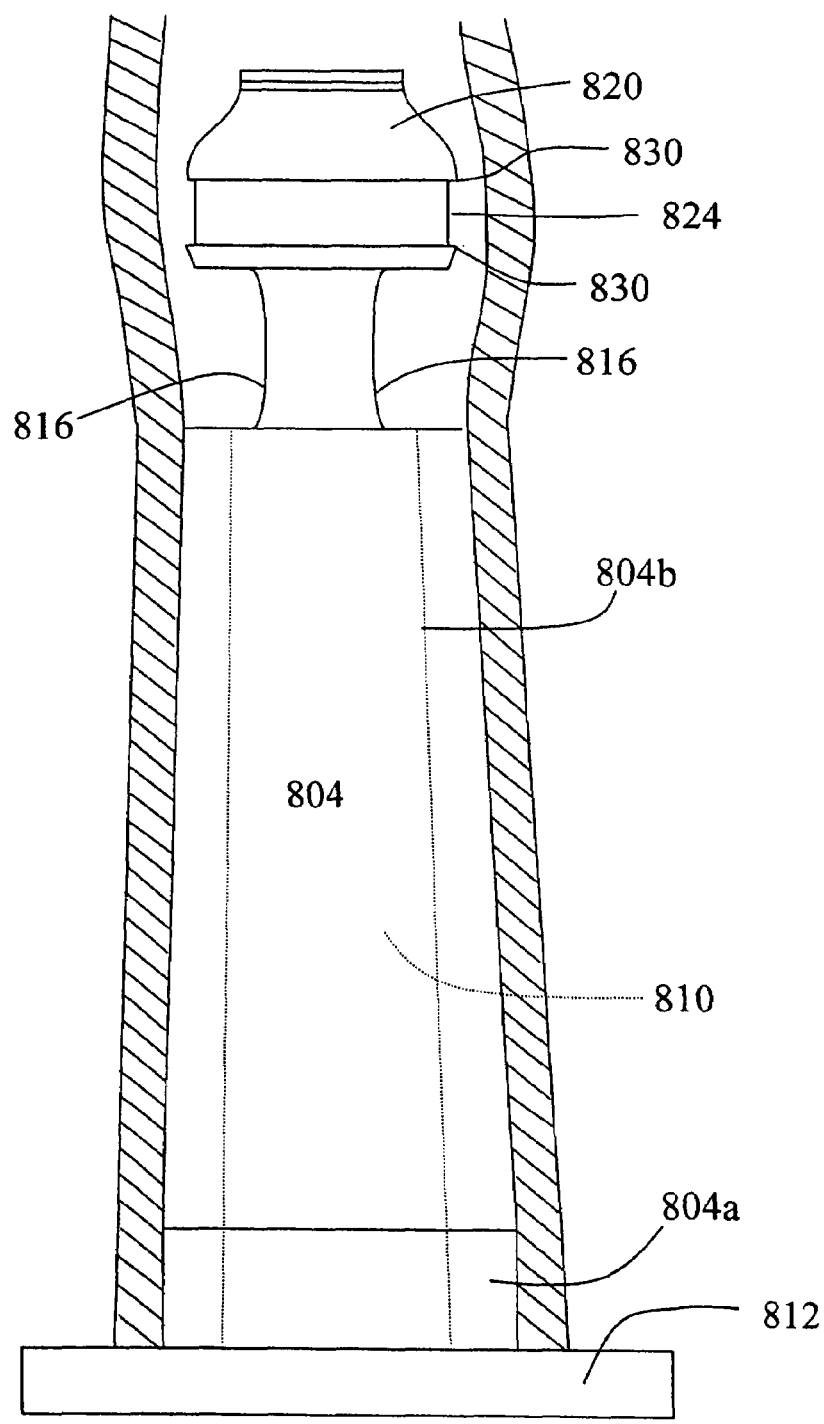

FIG. 15G shows yet another embodiment of the stop, indicated at 950. The stop 950 includes an inner portion 954 which is shaped with a configuration generally similar to the shape shown in FIG. 13A. An outer layer 958 is disposed on the inner portion 954 to thereby increase its diameter. The outer layer may be formed with ABS and solvent, or in a variety of other ways known to those of skill in the art.

While shown in FIG. 15G as covering the entire inner portion, those skilled in the art will appreciate that the stop 950 could be dipped once or repeatedly into a ABS solution to provide a variety of different shapes. Thus, for example, the inner layer could be covered half way to thereby form a sealing rib about the inner portion at a desired location. The stop 950 could be dipped repeatedly to form multiple sealing ribs, etc.

Figure 16:
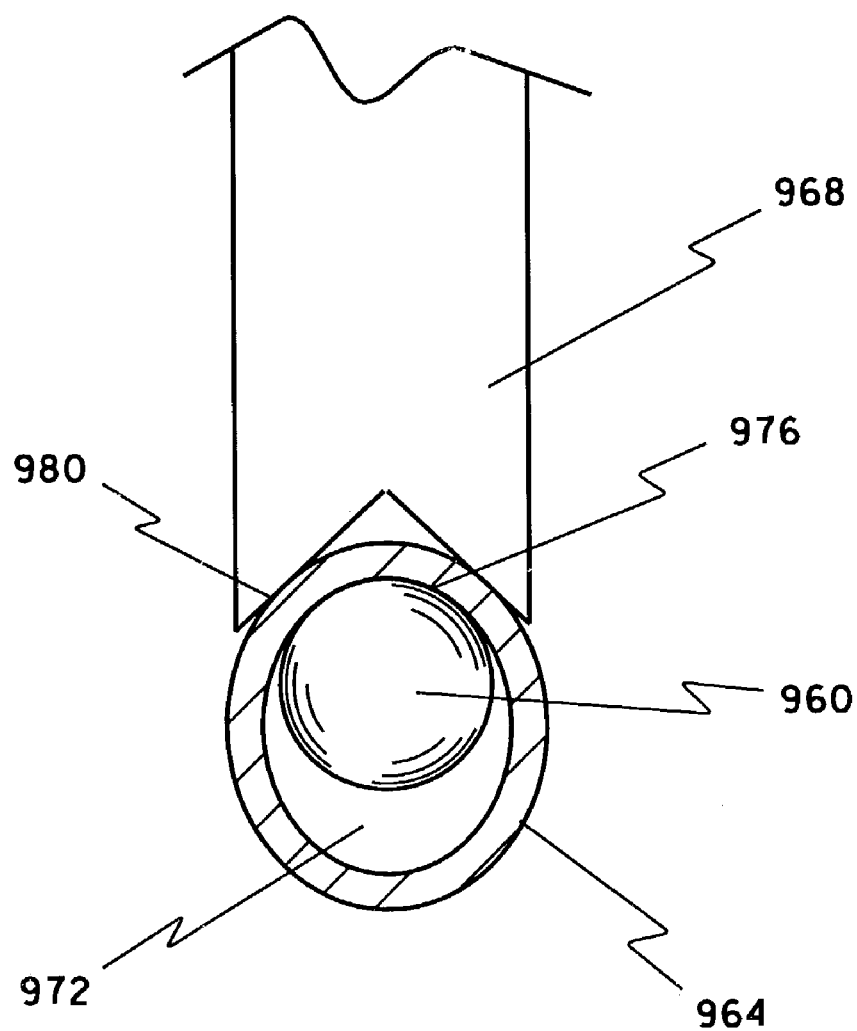
FIG. 16 shows a fragmented, side cross-sectional view of an infusion set with an occluder disposed therein and a control mechanism to maintain the infusion set and occluder in an open configuration.

Turning now to FIG. 16 there is shown a fragmented, side cross-sectional view of an infusion set with an occluder disposed therein. While FIGS. 5C–D and 9–11 above discuss embodiments wherein flow through the infusion set is enabled by compressing opposing sides of the tube against the occluder, it has been found in accordance with the present invention that a preferred configuration involves compressing the tube from generally one side to open a single fluid passage between the occluder and the tubing. Thus, as shown in FIG. 16, an occluder 960 is disposed in a tube 964. An actuator 968 is disposed to forcefully engage the tube 964 to open a fluid flow path 972 past the occluder.

The actuator 968 is configured to press on one side of the occluder, but not on both sides as discussed in the previous embodiments. The actuator 968 preferable has two engagement surfaces 976 and 980. The two engagement surfaces 976 and 980 are preferably spaced apart at an angle of less than 150 degrees, more preferably between about 90 and 135 degrees, and ideally about 110 degrees.

Because the engagement surfaces 976 and 980 of the actuator are offset but not opposite one another, the have a tendency to force the tubing in such a way that a single fluid flow channel 972 is formed passed the occluder 960. A single fluid flow channel 972 provides for more area and is less likely to be occluded by a viscous solution or a fibrous solution. When combined with the occluder configurations of FIGS. 14 and 15, the risk that the occluder will increase the risk of occlusion is significantly reduced. Furthermore, only requiring the movement of a single actuator decreases the complexity and cost of an enteral feeding pump.

Thus, there is disclosed an improved apparatus and method for preventing free flow in an infusion line. The apparatus and method can be used with infusion control pumps, such as enteral feeding pumps or IV pumps, or as a replacement for such pumps. While the present disclosure discloses embodiments which are currently preferred, those skilled in the art will appreciate numerous modifications which can be made without departing from the scope and spirit of the present invention. For example, the relative size of the infusion set and occluder could be changed by providing an occluder which shrinks sufficiently under pressure to create fluid flow passages. The appended claims are intended to cover such modifications.

What is claimed is:

1. An occluder for use in an infusion set, the occluder comprising:
   a body having a proximal section configured for disposition in a piece of tubing of an infusion set;
   a stop configured for positioning within the tubing of the infusion set;
   wherein fluid flow is accomplished by radial expansion of the tubing from fluid pressure in at least one portion of the tubing to enable flow around the stop;
   wherein the body has a channel therethrough for passing fluid and wherein the stop is attached to the body by at least one arm, the arm being disposed out of alignment with the channel; and
   wherein the at least one arm comprises a pair of arms spaced apart from each other and disposed generally opposite one another
   wherein the stop includes an inner portion and an outer layer attached to the inner portion.

2. An occluder for preventing fluid flow through a tube, the occluder comprising:
   a stop configured for disposal in the tubing, the stop comprising a sealing portion for engaging the tubing to prevent fluid flow between the stop and tubing until the tubing expands radially, wherein the sealing portion further comprises at least one projection extending from the sealing portion for sealing against the tubing; and
   a body having a channel formed therein for passing fluid therethrough, the body being attached to the stop by at least one arm disposed out of alignment with the channel in the body.

3. The occluder according to claim 2, wherein the sealing portion comprises a generally annular channel.

4. The occluder according to claim 2, wherein the sealing portion comprises at least one projection for sealing against the tubing which has a rounded shape.

5. The occluder according to claim 2, wherein the at least one projection comprises at least one annular bevel.

6. The occluder according to claim 2, wherein the at least one projection comprises a pair of spaced apart annular bevels.

7. The occluder according to claim 2, wherein the at least one projection comprises at least one annular rib.

8. The occluder according to claim 2, wherein the at least one projection comprises a pair of spaced apart annular ribs.

9. An occluder for use in an infusion set, the occluder comprising:
- a body having a proximal section configured for disposition in a piece of tubing of an infusion set;
- a stop configured for positioning within the tubing of the infusion set, the stop having at least one generally annular rib disposed thereon configured for engaging the piece of tubing to form a seal; and
- wherein fluid flow is accomplished by radial expansion of the tubing from fluid pressure in at least one portion of the tubing to enable flow past the stop and between the generally annular rib and the tubing.

10. The occluder according to claim 9, wherein the at least one generally annular rib comprises an annular bevel.

11. The occluder according to claim 10, wherein the at least one generally annular rib comprises a pair of bevels.

12. The occluder according to claim 11, wherein the bevels are separated by a generally annular channel.

13. The occluder according to claim 9, further comprising a first generally annular rib and a second generally annular rib.

14. The occluder according to claim 13, wherein the first generally annular rib and the second generally annular rib are spaced apart.

15. The occluder according to claim 13, wherein the first generally annular rib and the second generally annular rib extend radially outwardly to different degrees.

16. The occluder according to claim 13, wherein the first generally annular rib and the second generally annular rib extend radially outwardly substantially to the same extent.

17. An occluder for use in an infusion set, the occluder comprising:
- a body having a proximal section configured for disposition in a piece of tubing of an infusion set;
- a stop configured for positioning within the tubing of the infusion set, the stop having at least one generally annular rib disposed thereon configured for engaging the piece of tubing to form a seal;
- wherein fluid flow is accomplished by radial expansion of the tubing from fluid pressure in at least one portion of the tubing to enable flow between the generally annular rib and the tubing; and
- wherein the body has a channel therethrough for passing fluid and wherein the stop is attached to the body by at least one arm, the arm being disposed out of alignment with a channel through the body.

18. The occluder according to claim 17, wherein the at least one generally annular rib comprises two generally annular ribs.

19. The occluder according to claim 18, wherein the two generally annular ribs define a channel therebetween.

20. The occluder according to claim 17, wherein the portion of the stop proximal of the generally annular rib is tapered.

21. The occluder according to claim 17, wherein the proximal end of the stop defines a substantially planar surface disposes generally perpendicular to the long axis of the occluder.

* * * * *

UNITED STATES PATENT AND TRADEMARK OFFICE
CERTIFICATE OF CORRECTION

PATENT NO.       : 7,150,727 B2
APPLICATION NO.  : 10/317027
DATED            : December 19, 2006
INVENTOR(S)      : David Cise, David McNally and Kent F. Beck It is certified that error appears in the above-identified patent and that said Letters Patent is hereby corrected as shown below:

Figure 5A:
  It reads "100"; should read --300--
  It reads "100a"; should read --300a--

Figure 9:
  Reference 454 points to the infusion set, and should point to the occluder.

Figure 13A:
  It reads "724b"; should read --724a--

Figure 14A:
  Has a number "67" that is floating and unaffiliated.

Column 1:
  Line 17 and 18, read "...administration solutions through..."; should read --...administration of solutions through...--
  Line 56, it reads "...regulating device."; should read --...regulating devices.--

Column 3:
  Line 32, it reads "...embodiment of FIG. 3A..."; should read --...embodiment of FIG. 3B...--

Column 5:
  Line 49, it reads "...with a plurality rollers."; should read --...with a plurality of rollers.--

Column 6:
  Line 4, it reads "While the infusion set 22..."; should read --While the infusion set 10...--

Column 7:
  Line 14, it reads "...bag 18 may develop..."; should read --...bag 14 may develop...--
  Line 31, it reads "...the occluder 130 is..."; should read --...the occluder 104 is...--
  Line 39, it reads "...proximal end 138a..."; should read --...proximal end 138b...--
  Line 44, it reads "...proximal end 138a of the..."; should read --proximal end 138b of the...--
  Line 50, it reads "...the proximal end 138a..."; should read --...the proximal end 138b...--

UNITED STATES PATENT AND TRADEMARK OFFICE
CERTIFICATE OF CORRECTION

PATENT NO. : 7,150,727 B2
APPLICATION NO. : 10/317027
DATED : December 19, 2006
INVENTOR(S) : David Cise, David McNally and Kent F. Beck It is certified that error appears in the above-identified patent and that said Letters Patent is hereby corrected as shown below:

Column 8:
  Line 2, it reads "...another embodiment of principle of..."; should read --...another embodiment of...--

Column 9:
  Line 9, it reads "...distal end 208a..."; should read --...distal end 280a...--
  Line 10, it reads "...distal end 208a..."; should read --...distal end 280a...--
  Line 28, it reads "...above about 4 psi cause liquid..."; should read --above about 4 psi to cause liquid...--
  Line 45, it reads "...distal end 238b..."; should read --...distal end 234b...--

Column 10:
  Line 42, it reads "at 300, with an occluder 304..."; should read --at 100, with an occluder 100a...--
  Line 43, it reads "...infusion set 300 is made..."; should read --...infusion set 100 is made...--

Column 12:
  Line 64, it reads "...elongate tube 108..."; should read --...elongate tube 408...--

Column 14:
  Line 13, it reads "...down stream. The tethers..."; should read --...downstream. The tethers...--

Column 16:
  Line 32, it reads "...between the second actuator..."; should read --...between the second occluder..."

Column 17:
  Line 7, it reads "...the rotor 604 is..."; should read --...the rotor 612 is...--
  Line 52, it reads "...is used to connect to pieces of tubing..."; should read --...is used to connect two pieces of tubing...--
  Line 59, it reads "...tubing the proximal and/or distal..."; should read --...tubing along the proximal and/or distal...--

UNITED STATES PATENT AND TRADEMARK OFFICE
CERTIFICATE OF CORRECTION

PATENT NO. : 7,150,727 B2
APPLICATION NO. : 10/317027
DATED : December 19, 2006
INVENTOR(S) : David Cise, David McNally and Kent F. Beck It is certified that error appears in the above-identified patent and that said Letters Patent is hereby corrected as shown below:

Column 18:
 Line 1, it reads "...distal end 724a of the..."; should read --...distal end 724b of the...--
 Line 54, it reads "FIGS. 13D and 13E shown..."; should read --FIGS. 13D and 13E show...--
 Line 56, it reads "...pumps are portions of the..."; should read --...pumps and portions of the...--
 Line 57, it reads "...drawings are labeled according."; should read --pumps are labeled accordingly.--
 Line 60, it reads "the pump rotor 750 (FIG. 13D) and 760 (FIG. 13E)."; should read --the pump rotor 350 (FIG. 13D) and 612 (FIG. 13E).--
 Line 61, it reads "...pump rotor 750/760 rotates..."; should read --...pump rotor 350/612 rotates...--

Column 19:
 Line 1, it reads "...the need to recess an occiuder..."; should read --...the need to recess an occluder...--
 Line 22, it reads "...tubing the proximal and/or distal"; should read --...tubing along the proximal and/or distal--
 Line 26, it reads "Rather that being..."; should read --Rather than being...--
 Line 34, it reads "channel 790 in the..."; should read --channel or bore 790 in the...--
 Lines 43-44, they read "...which will open the valve to the flow..."; should read --which will open to the flow.--
 Lines 44-45, read "...which will open the valve to the flow..."; should read --...which will open to the flow...--

Column 20:
 Line 8, it reads "Attached to the proximal portion 804a..."; should read --Attached to the proximal portion 804b...--
 Line 40, it reads "...friction for the tubing 808..."; should read --...friction for the tubing 828...--
 Line 47, it reads "...500/1000 ths works significantly..."; should read --...500/1000 ths wide works significantly...--
 Line 48, it reads "...rounded stop of course, the..."; should read --...rounded stop. Of course, the...--

UNITED STATES PATENT AND TRADEMARK OFFICE
CERTIFICATE OF CORRECTION

PATENT NO. : 7,150,727 B2
APPLICATION NO. : 10/317027
DATED : December 19, 2006
INVENTOR(S) : David Cise, David McNally and Kent F. Beck It is certified that error appears in the above-identified patent and that said Letters Patent is hereby corrected as shown below:

Column 21:
 Line 11, references the "sealing area 882," which reference is not found on FIG. 15D.
 Line 17, it reads "...shape of the stop 870..."; should read --...shape of the stop 874...--
 Line 28, it reads "...curvature, if any of the..."; should read --...curvature, if any, of the...--
 Line 31, it reads "ribs, such as ribs..."; should read --ribs can be used, such as ribs...--
 Line 32, it reads "...in FIG. 15F. Thus..."; should read --...in FIG. 15F, may be used. Thus...--
 Line 65, it reads"...actuator 968 preferable has..."; should read --...actuator 968 preferably has...--

Column 22:
 Line 4, it reads "...one another, the have a..."; should read --...one another, they have a...--

Signed and Sealed this

Twenty-fourth Day of February, 2009

JOHN DOLL
*Acting Director of the United States Patent and Trademark Office*